(12) United States Patent
Sullenger et al.

(10) Patent No.: US 8,367,627 B2
(45) Date of Patent: Feb. 5, 2013

(54) FOCUSED LIBRARIES, FUNCTIONAL PROFILING, LASER SELEX, AND DESELEX

(75) Inventors: Bruce A. Sullenger, Chapel Hill, NC (US); Juliana M. Layzer, Durham, NC (US); Christopher P. Rusconi, Durham, NC (US); Sabah Oney, Durham, NC (US); Nanette L. S. Que-Gewirth, Buffalo, NY (US)

(73) Assignee: Duke University, Durham, NC (US)

( * ) Notice: Subject to any disclaimer, the term of this patent is extended or adjusted under 35 U.S.C. 154(b) by 998 days.

(21) Appl. No.: 11/992,125

(22) PCT Filed: Sep. 15, 2006

(86) PCT No.: PCT/US2006/036109
§ 371 (c)(1),
(2), (4) Date: Mar. 17, 2008

(87) PCT Pub. No.: WO2007/035532
PCT Pub. Date: Mar. 29, 2007

(65) Prior Publication Data
US 2009/0264508 A1    Oct. 22, 2009

Related U.S. Application Data

(60) Provisional application No. 60/716,935, filed on Sep. 15, 2005.

(51) Int. Cl.
*C07H 21/02* (2006.01)

(52) U.S. Cl. ............ 514/44 R; 536/23.1; 506/17; 506/26
(58) Field of Classification Search .................. None
See application file for complete search history.

(56) References Cited

U.S. PATENT DOCUMENTS

| | | | |
|---|---|---|---|
| 5,756,291 | A | 5/1998 | Griffin et al. |
| 6,376,190 | B1 | 4/2002 | Gold et al. |
| 6,855,496 | B2 | 2/2005 | Pagratis et al. |
| 2003/0175703 | A1 | 9/2003 | Sullenger et al. |
| 2005/0176940 | A1 | 8/2005 | King |

OTHER PUBLICATIONS

Int'l Search Report for PCT/US2006/036109, dated Sep. 5, 2007.
Written Opinion for PCT/US2006/036109, dated Sep. 5, 2007.

*Primary Examiner* — Christopher M Gross
(74) *Attorney, Agent, or Firm* — Nixon & Vanderhye P.C.

(57) ABSTRACT

Focused aptamer libraries are constructed in accordance with a proteome (i.e., complex mixture of native biomolecules). The libraries may be screened to identify one or more candidate aptamers with desired biological activities other than specific binding to a target. Aptamers which are selected or derivatives thereof may be used for those specific activities in biological systems. Any combination of deconvoluting a focused library (functional profiling), increasing frequencies of particular aptamers in a focused library (Laser SELEX), and decreasing frequencies of particular aptamers in a focused library (DeSELEX) may be performed prior to assaying biological activity.

9 Claims, 18 Drawing Sheets

RNA Pools Inhibit Platelet Function in a PFA Assay

| Sample | Mean Closing Time (CT), sec |
|---|---|
| Buffer | 103 |
| Positive Control | >300 |
| Activated RNA, 1 μM | |
| AR5 | 249 |
| AR6 | >300 |
| AR7 | >300 |
| AR8 | >300 |
| AR9 | >300 |
| Unstimulated RNA, 1 μM | |
| U6 | >300 |
| U7 | >300 |
| U8 | 200 |
| Negative/Positive RNA, 1 μM | |
| PN6 | >300 |
| PN8 | >300 |

Selection against Unstimulated Platelets

FOCUSED LIBRARIES, FUNCTIONAL PROFILING, LASER SELEX, AND DESELEX

CROSS REFERENCE TO RELATED APPLICATION

This application is a U.S. national stage under 35 U.S.C. 371 of Int'l Application No. PCT/US2006/036109, filed Sep. 15, 2006; which claims priority benefit of provisional U.S. Application No. 60/716,935, filed Sep. 15, 2005; the disclosures of which are incorporated by reference herein.

FEDERALLY-SPONSORED RESEARCH OR DEVELOPMENT

The U.S. Government has certain rights in this invention as provided for by the terms of NIH-RO1-HL65222 from the Department of Health and Human Services.

FIELD OF THE INVENTION

The invention relates to methods for constructing focused aptamer libraries in accordance with a proteome (i.e., a complex mixture of native biomolecules). Libraries may be screened to isolate one or more aptamers with a desired biological activity other than simply binding to a target biomolecule. Focused libraries, aptamers that are isolated by such methods or their derivatives, and use of aptamers in biological systems are provided thereby. The invention also relates to methods for deconvolution of a focused library by functional profiling of its members using one or more assays to determine each member's biological activity, increasing frequencies in a focused library of particular members by Laser SELEX, decreasing frequencies in a focused library of particular members by DeSELEX, or any combination thereof.

BACKGROUND OF THE INVENTION

Systematic evolution of ligands by exponential enrichment (SELEX) has been used to select one or more single-stranded nucleic acids which specifically bind a target (Tuerk & Gold, Science 249:505-510, 1990; Ellington & Szostak, Nature 346:818-822, 1990). Such nucleic acids are called aptamers. An aptamer, which antagonizes the activity of vascular endothelial growth factor (VEGF), is used to treat age-related macular degeneration.

U.S. Pat. No. 5,270,163 describes the SELEX method. A library of nucleic acids is contacted with a target, and those nucleic acids specifically bound to the target are partitioned from the remainder of nucleic acids in the library which do not specifically bind the target. The partitioned nucleic acids are amplified to yield a ligand-enriched pool. Multiple cycles of binding, partitioning, and amplifying (i.e., selection) result in identification of one or more aptamers with the desired activity. The typical library is constructed with many nucleic acids of different sequences that confer structurally diverse conformations so selection of the desired nucleic acid(s), which are present at low frequency in the library, can be difficult.

U.S. Pat. No. 6,376,190 describes increasing or decreasing frequency of nucleic acids in a library by their binding to a chemically synthesized peptide. This method requires a purified or recombinant (i.e., non-native) target for binding to members of the library. It teaches away from enriching for particular members of a library using a complex mixture of proteins in more than two rounds. See columns 9 to 16.

It would be convenient if a library containing candidate aptamers could be focused against a proteome (i.e., complex mixture of native biomolecules) over multiple rounds of binding, partitioning, and amplifying. In accordance with the present invention, focusing increases the fraction of nucleic acids binding to the native biomolecules (e.g., randomized sequences which are present in substantially equal abundance tend to frequencies reflecting strength of target binding and abundance of targets in the proteome) and decreases the fraction of nucleic acids in the library which do not bind to the proteome. Sequence complexity of the library (i.e., number of different nucleic acids according to their sequences) and the size of library (i.e., total number of nucleic acids) are reduced by focusing. Individual members that would otherwise tend to predominant the focused library because of strong target binding and high target abundance in the proteome may mask the relatively less abundant (i.e., scarce) candidate aptamers in the library and prevent their isolation. In accordance with the present invention, frequently isolated members of a library may be depleted therefrom as they are identified by their sequences.

Therefore, it is an objective(s) of the invention to provide improved methods for SELEX, focused libraries of reduced complexity and enhanced relevancy to intended targets, easier and more efficient screening of focused libraries, or aptamers with desired biological activity other than target binding. Long-felt needs are addressed thereby.

The present invention is also directed to an improvement(s) in SELEX to construct focused libraries, deconvoluting libraries by one or more functional (i.e., non-binding) assays, increasing frequencies of one or more candidate aptamers which bind to native targets of a proteome, decreasing frequencies of one or more candidate aptamers which bind to native targets of a proteome, or any combination thereof that address the aforementioned problems. Methods for using and making these products (i.e., focused libraries, aptamers, and derivatives thereof) are provided. Further objectives and advantages of the invention are described below. Other advantages and improvements are described below or would be apparent from the disclosure herein.

SUMMARY OF THE INVENTION

It is an objective to construct a library of candidate aptamers. The library may be constructed by providing an initial collection of single-stranded nucleic acids, contacting the collection with a mixture of native biomolecules (e.g., proteome of a body fluid, cultured cell, or tissue; or a fractionated portion thereof) under binding conditions, partitioning between nucleic acids which are bound to targets in the mixture and nucleic acids which do not bind, amplifying target-bound nucleic acids, and repeating as desired with target-bound nucleic acids being used as another collection of single-stranded nucleic acids until a decreased number of different candidate aptamers results in the focused library. Alternatively, partitioning may be negative selection with the mixture.

The library may be deconvoluted into sublibraries by arraying, labeling, or functional profiling by a biological assay (not only specifically binding to target) the individual members of the focused library. Individual candidate aptamers may be isolated and sequenced before assaying biological activities of the nucleic acids.

Laser SELEX is a method for increasing the frequency of a selected candidate aptamer in a focused library by contacting single-stranded nucleic acids of the library with one or more isolated biomolecules (e.g., artificially synthesized or recombinant polypeptide) or a mixture of native biomolecules under binding conditions, partitioning between nucleic acids which are bound to targets and nucleic acids which did not bind to targets, amplifying target-bound nucleic acids, and repeating with target-bound nucleic acids being used in another round until the frequency of the selected candidate aptamer able to bind target biomolecules is increased as desired DeSELEX is a method for decreasing the frequency of a deselected candidate aptamer in a focused library by contacting single-stranded nucleic acids of the library with one or more complementary nucleic acids (e.g., oligonucleotide). Stringent hybridization between nucleic acids of the focused library and the complementary nucleic acids depletes the deselected candidate aptamer (usually high frequency sequences which predominate in the focused library) before they are able to bind with target biomolecules.

Focused libraries (with or without deconvolution, enrichment by Laser SELEX, depletion by DeSELEX, or any combination thereof) may be screened by binding a pool of candidate aptamers to a target and/or functionally assaying biological activity. Aptamers may be selected by such screening. The isolated aptamers may be identified by sequencing. Aptamers include those comprised of the sequences disclosed herein. Aptamers may be formulated in a composition with vehicle, and optional carrier(s) or excipient(s). Therefore, aptamers may be used to affect biological properties in vitro or in vivo. Their effects may be at least modulated with an oligonucleotide of complementary sequence. Aptamers may be used as medicaments for a subject in need of treatment or modulators (e.g., promote or inhibit) of biochemical reactions.

Further aspects of the invention will be apparent to a person skilled in the art from the following description of specific embodiments and generalizations thereto.

BRIEF DESCRIPTION OF THE DRAWINGS

FIG. 7 shows selection of nucleic acids in the focused library against thrombin-activated platelets. An increase in binding affinities and fraction of RNA bound (FB) was observed within several rounds of selection (focusing).

DESCRIPTION OF SPECIFIC EMBODIMENTS OF THE INVENTION

Figure 1:
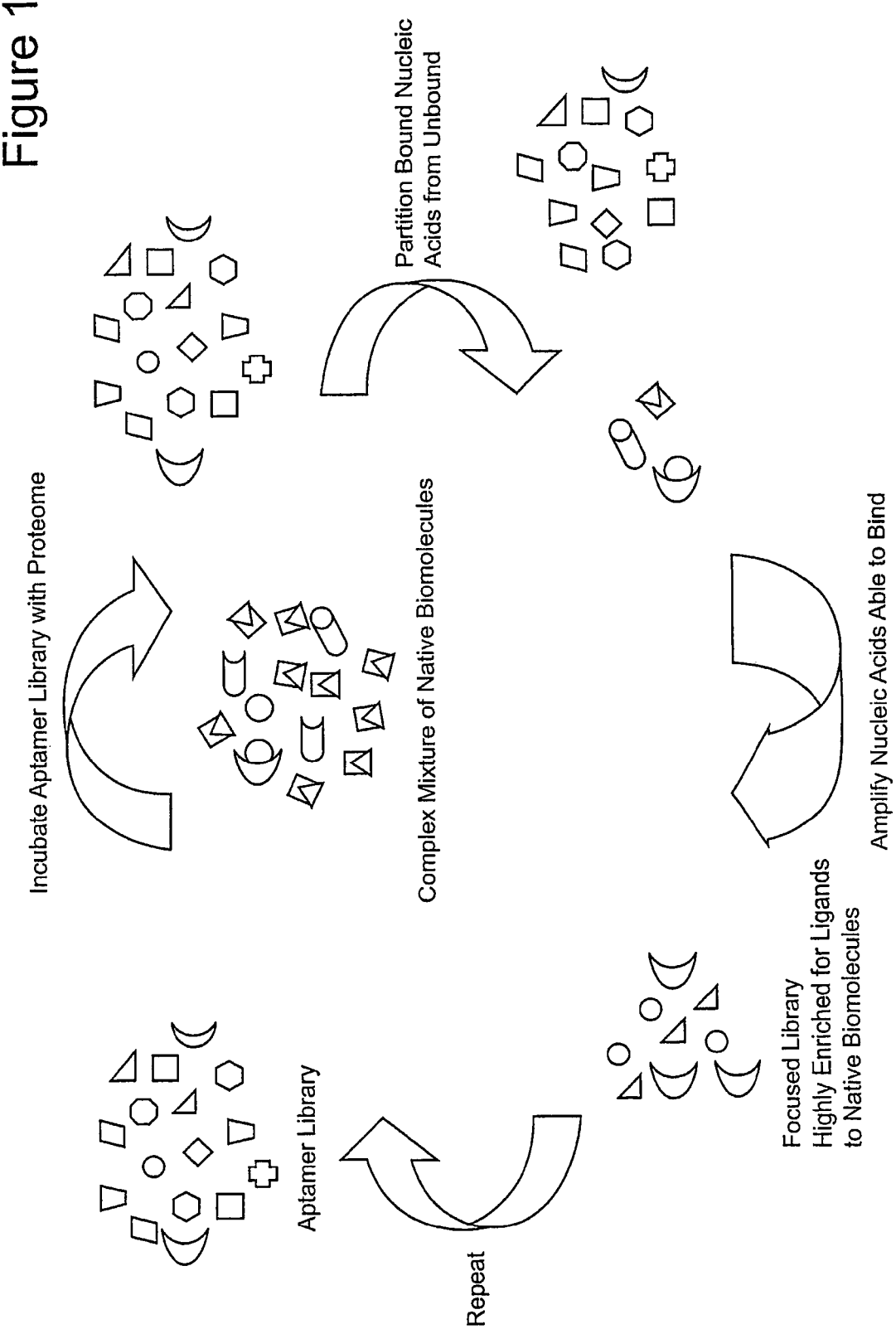
FIG. 1 illustrates a schematic for the construction of a focused library, which is comprised of aptamers having diverse sequences, against a complex mixture of different native biomolecules (e.g., a proteome).

A focused library or several sublibraries of candidate aptamers can be constructed by providing an initial collection of single-stranded nucleic acids (e.g., DNA, RNA, or variants thereof), contacting the collection with a mixture of native biomolecules (e.g., proteome of a body fluid, cultured cell, or tissue; or a fractionated portion thereof) under binding conditions, partitioning between nucleic acids which are bound to targets in the mixture and nucleic acids which do not bind, amplifying target-bound nucleic acids, and repeating as desired with target-bound nucleic acids being used as another collection of single-stranded nucleic acids until a decreased number of different candidate aptamers results in the focused library. In one or more rounds, partitioning may be negative selection against another mixture of native biomolecules.

Multiple rounds of binding, partitioning, and amplifying (e.g., at least 5, at least 10, at least 20, at least 30, at least 40, or at least 50 rounds) under similar or different binding conditions in each round may decrease the number of different nucleic acids (e.g., starting from at least $10^{10}$, at least $10^{11}$, at least $10^{12}$, at least $10^{13}$, at least $10^{14}$, or at least $10^{15}$ different nucleic acids) in the initial collection to result in the focused library (e.g., ending at most $10^2$, at most $10^3$, at most $10^4$, at most $10^5$, or at most $10^6$ different nucleic acids).

Aptamers of identical sequence may comprise at least 0.01%, at least 0.05%, at least 0.1%, at least 0.5%, at least 1%, at least 5%, or at least 10% of the focused library. Abundance of aptamers may be increased or decreased in their frequency before initial screening by binding to a specific target or after isolation of candidate aptamers. Therefore, in contrast to the prior art, focused libraries will be comprised of candidate aptamers which are reduced by a factor of at least $10^{-4}$, at least $10^{-5}$, at least $10^{-6}$, at least $10^{-7}$, at least $10^{-8}$, at least $10^{-9}$, at least $10^{-10}$, at least $10^{-11}$, at least $10^{-12}$, or at least $10^{-13}$ as compared to the complete sequence diversity of the initial collection of nucleic acids.

The library may be deconvoluted into sublibraries by arraying, labeling, or functional profiling by a biological assay (not only specifically binding to target) the individual members of the focused library. Individual candidate aptamers may be isolated (e.g., manual or automated robotic picking of clones) and sequenced before assaying biological activities of the nucleic acids.

Laser SELEX is a method for increasing the frequency of a selected candidate aptamer in a focused library by contacting single-stranded nucleic acids of the library with one or more isolated biomolecules (e.g., artificially synthesized or recombinant polypeptide) or a mixture of native biomolecules under binding conditions, partitioning between nucleic acids which are bound to targets and nucleic acids which did not bind to targets, amplifying target-bound nucleic acids, and repeating with target-bound nucleic acids being used in another round until the frequency of the selected candidate aptamer able to bind target biomolecules is increased as desired. Abundance of identical aptamers may be increased to a frequency of at least 0.01%, at least 0.05%, at least 0.1%, at least 0.5%, at least 1%, at least 5%, or at least 10% of the library.

DeSELEX is a method for decreasing the frequency of a deselected candidate aptamer in a focused library by contacting single-stranded nucleic acids of the library with one or more complementary nucleic acids (e.g., oligonucleotide). Stringent hybridization between nucleic acids of the focused library and the complementary nucleic acids depletes the deselected candidate aptamer (usually high frequency sequences which predominate in the focused library) before they are able to bind with target biomolecules. Here, in contrast to Laser SELEX, abundance of any aptamer in the library may be decreased to a frequency of at most 0.001%, or at most 0.005%, at most 0.01%, at most 0.05%, at most 0.1%, at most 0.5%, or at most 1%.

A subtractive library may be constructed using proteomes from two or more related states (e.g., active vs. inactive, aged vs. young, cancerous vs. noncancerous, differentiated vs. undifferentiated, diseased vs. healthy, induced vs. uninduced, mutant vs. wildtype). Single-stranded nucleic acids may be enriched for one status using Laser SELEX and/or depleted for the other status using DeSELEX.

Focused libraries (with or without deconvolution, enrichment by Laser SELEX, depletion by DeSELEX, or any combination thereof) may be screened by binding a pool of candidate aptamers to a target and/or functionally assaying biological activity. Aptamers may be selected by such screening. The isolated aptamers may be identified by sequencing. They may be amplified and inserted into transfer vectors.

Derivative aptamers with similar biological activity and improved properties like ease in manufacture (e.g., avoidance of premature termination or solubility), half-life in circulation (i.e., bioavailability), and resistance to degradation (i.e., stability) may be produced by artificial synthesis (e.g., solid-phase chemistry) with optional use of modified base, sugar, and/or phosphodiester linkage. The sequence of the selected aptamer may be inserted in a related aptamer with blocked ends, attachment to a polyethylene glycol (PEG) or cholesterol, or duplexed strands. Derivative aptamers include those comprised of the sequences disclosed herein. Aptamers may be formulated in a composition with vehicle, and optional carrier(s) or excipient(s).

Therefore, aptamers may be used to affect biological properties in vitro or in vivo. Their effects may be at least modulated with an oligonucleotide of complementary sequence. Aptamers may be used as medicaments for a subject in need of treatment or modulators (e.g., promote or inhibit) of biochemical reactions.

Additionally, one or more members of the focused library may be isolated as individual aptamers in liquid placed in wells of a plate array or labeled containers, dried on spots of a patterned substrate, or attached to coded particles. Because of the reduced complexity of the library, deconvolution of the library into individual members or small pools thereof is practical and allows screening using biological assays (especially high throughput screens).

Figure 2:
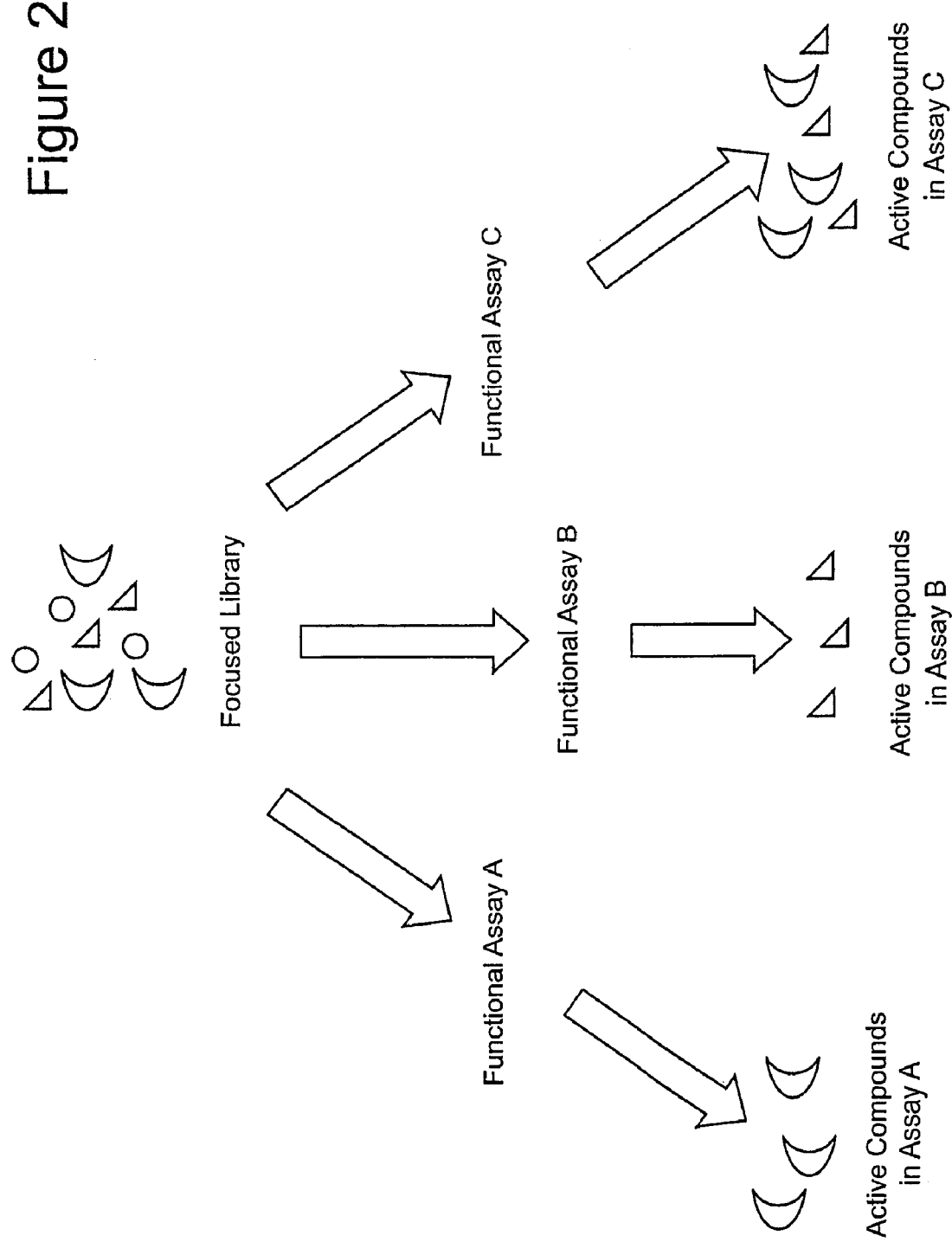
FIG. 2 illustrates a schematic for functional profiling used for deconvolution of a focused library: assay A, B or C used to isolate lead compounds with desired biological activities.
Figure 3:
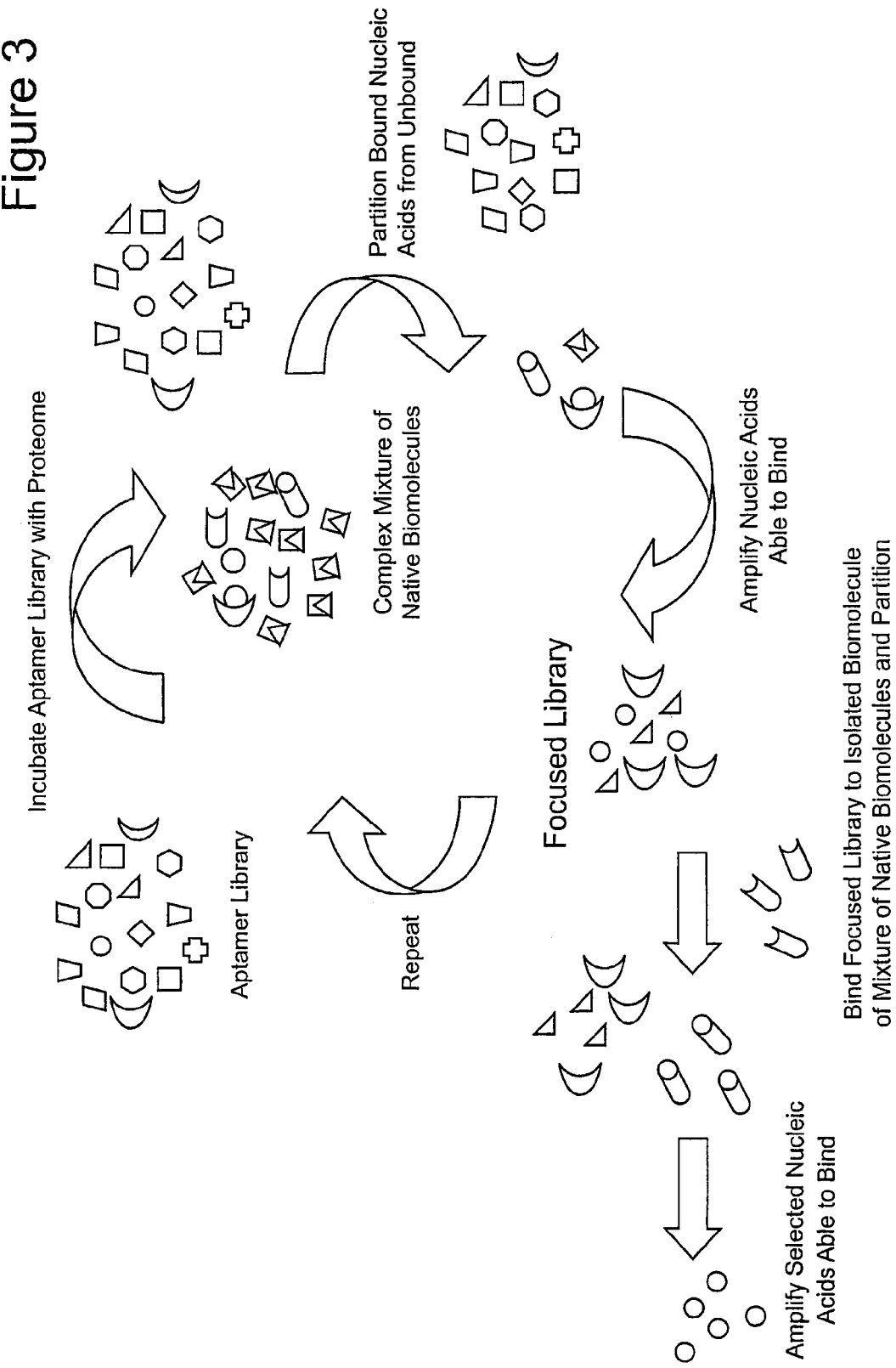
FIG. 3 illustrates a schematic for Laser SELEX to enrich (e.g., select) for candidate aptamers from a focused library.
Figure 4:
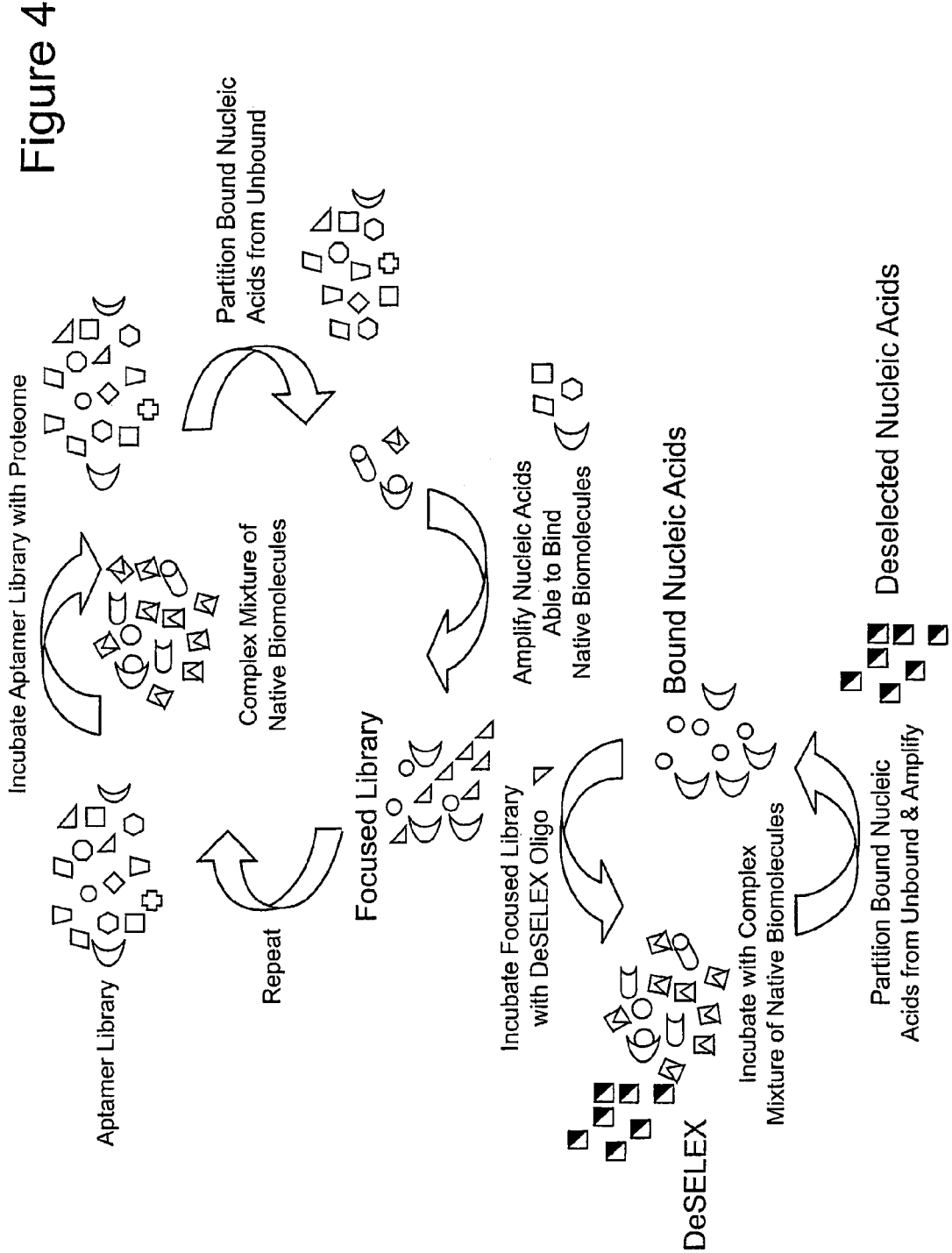
FIG. 4 illustrates a schematic for DeSELEX to deplete (e.g., deselect) candidate aptamers from a focused library with at least one complementary nucleic acid (e.g., oligonucleotide). Prior binding between members of the library and complementary nucleic acids (i.e., hybridization) prevents later binding between candidate aptamers and targets.

We have developed a novel and highly useful approach for isolating aptamers against targets of interest. The SELEX methodology has been utilized by us and others to identify nucleic acid aptamers to a number of purified protein targets. In this approach a large library of random RNAs (usually greater than $10^{14}$ or $10^{15}$) are mined for those rare nucleic acids (e.g., DNA, RNA, or variants thereof) that bind to a purified target. Since this method requires that one reduce the complexity of the library from such a great number to those few compounds of interest this method takes multiple rounds of iterative binding and purification. Here, we describe how one can generate a focused library of aptamers that is greatly enriched for those nucleic acids that bind proteins present in a mixture of targets (or proteome) (FIG. 1). Since this focused library is much smaller in complexity than a normal starting SELEX library, the aptamers present in the focused library can be screened in functional assays to determine which of the RNAs have the activity desired, a method we have termed functional profiling (FIG. 2). Then these aptamers can be employed as affinity ligands to purify and identify the target that they interact with in the proteome. In addition, selection is greatly facilitated using a focused library that contains a target of interest since the complexity of the library has been already greatly reduced (FIG. 3). Finally, we developed a method termed DeSELEX to decrease the frequency of nucleic acids that may start to predominant during focusing of the library (FIG. 4). Using this method, one can mine the sequences in the focused library more deeply since already identified ligands can be purged from the library.

Thus focused RNA libraries can greatly facilitate the generation of aptamers against a variety of targets. We have exemplified the invention by generating and utilizing focused libraries against the GLA-protein fraction of human plasma proteins, total human plasma proteins, and cell surface targets on both activated and unactivated human platelets.

We describe aptamers (preferably modified RNA) which modulate (preferably inhibit) the biological activities of Factor VII, Factor IX, Factor X, and von Willebrand factor (VWF). Aptamers in the examples are comprised of 2'-fluoro-pyrimidines and 5-hydroxy-purines. Other modifications can be made such as substitution with 2'-O-methyl nucleotides after isolation of an aptamer to provide a derivative thereof. The affinities of the aptamers for their targets may range from a $K_d$ of at least 10 pM, at least 100 pM, at least 1 nM, or at least 10 nM. Moreover, aptamers can act as competitive inhibitors and block the biological activity of plasma biomolecules, platelet biomolecules, and GLA proteins in enzymatic assays. Furthermore, aptamers can act as potent anti-coagulants and significantly delay the clotting time of normal human plasma or the activation of platelets in response to thrombin.

The following terms are believed to have well-recognized meanings in the art. But the following definitions are set forth to facilitate describing the invention.

As used herein, a "target" or "target biomolecule" refers to a biomolecule that could be the focus of a therapeutic drug strategy or diagnostic assay, including, without limitation, proteins or portions thereof, enzymes, peptides, enzyme inhibitors, hormones, carbohydrates, glycoproteins, lipids, phospholipids, nucleic acids, and generally, any biomolecule capable of turning a biochemical pathway on or off or modulating it, or which is involved in a predictable biological response. Targets can be free in solution, like thrombin, or associated with cells or viruses, as in receptors or envelope proteins. Any ligand that is of sufficient size to be specifically recognized by an oligonucleotide sequence can be used as the target. Thus, glycoproteins, proteins, carbohydrates, membrane structures, receptors, organelles, and the like can be used as the complexation targets.

A wide variety of materials can serve as targets. These materials include intracellular, extracellular, and cell surface proteins, peptides, glycoproteins, carbohydrates, including glycosaminoglycans, lipids, including glycolipids, and certain oligonucleotides.

The term "ligand" as used herein refers to a molecule or other chemical entity having a capacity for binding to a target. A ligand can comprise a peptide, an oligonucleotide, a nucleic acid (e.g., aptamer), a small chemical molecule, an antibody or fragment thereof, nucleic acid-protein fusion, and/or any other affinity agent. Thus, a ligand can come from any source, including libraries, particularly combinatorial libraries, such as the aptamer libraries disclosed herein below, phage display libraries, or any other library as would be apparent to one of ordinary skill in the art after review of the disclosure of the present invention presented herein.

The term "nucleic acid" is meant to refer to a polymeric molecule, which in addition to containing ribonucleosides or deoxyribonucleosides as bases, may also contain at least one of the following: 2'-deoxy, 2'-halo (including 2'-fluoro), 2'-amino (preferably not substituted or mono- or disubstituted), 2'-mono-, di- or trihalomethyl, 2'-O-alkyl, 2'-O-halo-substituted alkyl, 2'-alkyl, azido, phosphorothioate, sulfhydryl, methylphosphonate, fluorescein, rhodamine, pyrene, biotin, xanthine, hypoxanthine, 2,6-diamino purine, 2-hydroxy-6-mercaptopurine and pyrimidine bases substituted at the 6-position with sulfur or 5-position with halo or $C_{1-5}$ alkyl groups, abasic linkers, 3'-deoxy-adenosine as well as other available "chain terminator" or "non-extendible" analogs (at the 3'-end of the nucleic acid), or labels such as $^{32}P$, $^{33}P$, $^{35}S$, and the like. All of the foregoing can be incorporated into a nucleic acid using the standard synthesis techniques disclosed herein.

The terms "binding activity" and "binding affinity" are meant to refer to the tendency of a ligand molecule to bind or not to bind to a target. The energetics of said interactions are significant in "binding activity" and "binding affinity" because they define the necessary concentrations of interacting partners, the rates at which these partners are capable of associating, and the relative concentrations of bound and free molecules in a solution. The energetics are characterized herein through, among other ways, the determination of a dissociation constant, $K_d$. Preferably, the $K_d$ is established using a double-filter nitrocellulose filter binding assay such as that disclosed by Wong & Lohman (Proc. Natl. Acad. Sci. USA 90, 5428-5432, 1993). Every more preferably, an aptamer having a preferred $K_d$ value is further assayed for effects on the target (e.g., modulating one or more of the target's biological activities). For example, a $K_i$ value as described herein below can be determined for the aptamer and the target.

As used herein, "specifically binding oligonucleotides", "nucleic acid ligands" or "aptamers" refer to oligonucleotides having specific binding regions that are capable of forming complexes with an intended target in an environment herein other substances in the same environment are not complexed to the oligonucleotide. The specificity of the binding is defined in terms of the comparative dissociation constants ($K_d$) of the aptamer for target as compared to the dissociation constant with respect to the aptamer and other materials in the environment or unrelated molecules in general. Typically, the $K_d$ for the aptamer with respect to the target will be 2-fold, preferably 5-fold, more preferably 10-fold less than $K_d$ with respect to target and the unrelated material or accompanying material in the environment. More preferably, the $K_d$ will be 50-fold less, even more preferably 100-fold less, and yet more preferably 200-fold less.

The binding affinity of the aptamers herein with respect to targets and other molecules is defined in terms of $K_d$. The value of this dissociation constant can be determined directly by well-known methods, and can be computed even for complex mixtures by methods such as those, for example, set forth in Caceci et al. (Byte 9:340-362, 1984). It has been observed, however, that for some small oligonucleotides, direct determination of $K_d$ is difficult, and can lead to misleadingly high results. Under these circumstances, a competitive binding assay for the target or other candidate substance can be conducted with respect to substances known to bind the target or candidate. The value of the concentration at which 50% inhibition occurs ($K_i$) is, under ideal conditions, equivalent to $K_d$. However, in no event will a $K_i$ be less than $K_d$. Thus, determination of $K_i$, in the alternative, sets a maximal value for the value of $K_d$. Under those circumstances where technical difficulties preclude accurate measurement of $K_d$, measurement of $K_i$ can conveniently be substituted to provide an upper limit for $K_d$. A $K_i$ value can also be used to confirm that an aptamer of the present binds a target.

In general, aptamers may comprise from 10 to 100 nucleotides, from 15 to 40 nucleotides, or from 20 to 40 nucleotides, in that oligonucleotides of a length that falls within these ranges are readily prepared by conventional techniques. Optionally, aptamers can further comprise a minimum of five, 10 or 15 nucleotides that are necessary to effect specific binding. The only apparent limitations on the binding specificity concern sufficient sequence to be distinctive in the nucleic acid and sufficient binding capacity of the target to obtain the necessary interaction. Aptamers of binding regions containing sequences shorter than 10, e.g., 5-mers, are feasible if the appropriate interaction can be obtained in the context of the environment in which the target is placed. Thus, if there is little interference by other materials, less specificity and less strength of binding can be required.

As used herein, "aptamer" refers in general to either an oligonucleotide of a single defined sequence or a mixture of said oligonucleotides, wherein the mixture retains the properties of binding specifically to the target. Thus, as used herein "aptamer" denotes both singular and plural sequences of oligonucleotides, as defined hereinabove. The term "aptamer" is meant to refer to a single- or double-stranded nucleic acid which is capable of binding to a protein or other molecule, and thereby disturbing the protein's or other molecule's function.

Structurally, the aptamers may be specifically binding oligonucleotides, wherein "oligonucleotide" is as defined herein. As set forth herein, oligonucleotides include not only those with conventional bases, sugar residues and internucleotide linkages, but also those that contain modifications of any or all of these three moieties.

"Single-stranded" oligonucleotides, as the term is used herein, refers to those oligonucleotides that contain a single covalently linked series of nucleotide residues.

"Oligos" or "oligonucleotides" include nucleic acid (DNA, RNA, or analogs thereof) sequences of more than one nucleotide in either single chain or duplex form and specifically includes short sequences such as dimers and trimers, in either single chain or duplex form, which can be intermediates in the production of the specifically binding oligonucleotides. "Modified" forms used in candidate pools contain at least one non-native residue.

"Oligonucleotide" or "oligomer" is generic to polydeoxyribonucleotides (containing 2'-deoxy-D-ribose or modified forms thereof, i.e., DNA, to polyribonucleotides (containing D-ribose or modified forms thereof, i.e., RNA, and to any other type of polynucleotide which is an N-glycoside or C-glycoside of a purine or pyrimidine base, or modified purine or pyrimidine base or abasic nucleotides.

An "RNA aptamer" is an aptamer comprising ribonucleoside units. "RNA aptamer" is also meant to encompass RNA analogs as defined herein above.

The term "coagulation factor aptamer" is meant to refer to a single- or double-stranded nucleic acid that binds a coagulation factor and modulates its function. The term "coagulation factor" is meant to refer to a factor that acts in either or both of the intrinsic and the extrinsic coagulation cascade.

When a number of individual, distinct aptamer sequences for a single target have been obtained and sequenced as described above, the sequences can be examined for "consensus sequences". As used herein, "consensus sequence" refers to a nucleotide sequence or region (which might or might not be made up of contiguous nucleotides) that is found in one or more regions of at least two aptamers, the presence of which can be correlated with aptamer-to-target-binding or with aptamer structure.

A consensus sequence can be as short as three nucleotides long. It also can be made up of one or more noncontiguous sequences with nucleotide sequences or polymers of hundreds of bases long interspersed between the consensus sequences. Consensus sequences can be identified by sequence comparisons between individual aptamer species, which comparisons can be aided by computer programs and other tools for modeling secondary and tertiary structure from sequence information. Generally, the consensus sequence will contain at least three to 20 nucleotides, more commonly from six to ten nucleotides.

As used herein, "consensus sequence" means that certain positions, not necessarily contiguous, of members of the library are specified. By "specified" it is meant that the composition of the position is other than completely random (e.g., equal likelihood of being any one of four nucleotides). All members of the library cannot have the same nucleotide at such position; for example, the consensus sequence can contain a known ratio of particular nucleotides. For example, a consensus sequence might consist of a series of four positions wherein the first position in all members of the library is adenosyl (rA), the second position is 25% adenosyl (rA), 35% uracyl (U) and 40% cytosyl (rC), the third position is uracyl (U) in all oligonucleotides, and the fourth position is guanosyl (rG) in 50% of the members and cytosyl (rC) in 50% of the members.

When a consensus sequence is identified, oligonucleotides that contain that sequence can be made by conventional synthetic or recombinant techniques. These aptamers can also function as target-specific aptamers. Such an aptamer can conserve the entire nucleotide sequence of an isolated aptamer, or can contain one or more additions, deletions, or substitutions in the nucleotide sequence, as long as a consensus sequence is conserved. A mixture of such aptamers can also function as target-specific aptamers, wherein the mixture is a set of aptamers with a portion or portions of their nucleotide sequence being random or varying, and a conserved region that contains the consensus sequence. Additionally, secondary aptamers can be synthesized using one or more of the modified bases, sugars, and linkages described herein using conventional techniques and those described herein.

Aptamers can be sequenced or mutagenized to identify consensus regions or domains that are participating in aptamer binding to target, and/or aptamer structure. This information is used for generating second and subsequent pools of aptamers of partially known or predetermined sequence. Sequencing used alone or in combination with the retention and selection processes, can be used to generate less diverse oligonucleotide pools from which aptamers can be made. Further selection according to these methods can be carried out to generate aptamers having preferred characteristics for diagnostic or therapeutic applications. That is, domains that facilitate, for example, drug delivery could be engineered using the aptamers.

Although an objective is to isolate aptamers from pools of focused libraries, it also can be used to deconvolute libraries into known or partially known individual aptamers or pools of aptamers (i.e., their sequences are known). A pool is considered diverse even if one or both ends of the oligonucleotides comprising it are not identical from one pool member to another, or if one or both ends of the oligonucleotides comprising the pool are identical with non-identical intermediate regions from one pool member to another. Toward this objective, knowledge of the structure and organization of the target can be useful to distinguish features that are important for modulation of a biochemical pathway or biological response generation in the first generation aptamers.

Those skilled in the art will appreciate that comparisons of the complete or partial amino acid sequences of the purified target to identify variable and conserved regions is useful. Comparison of sequences of aptamers provides information about the consensus regions and consensus sequences responsible for binding. It is expected that certain nucleotides will be rigidly specified and certain positions will exclusively require certain bases. Likewise, studying localized regions of a protein to identify secondary structure can be useful. Localized regions of a protein can adopt a number of different conformations including beta strands, alpha helices, turns (induced principally by proline or glycine residues), or random structure. Different regions of a polypeptide interact with each other through hydrophobic and electrostatic interactions and also by formation of salt bridges, disulfide bridges, etc. to form the secondary and tertiary structures. Defined conformations can be formed within the protein organization, including beta sheets, beta barrels, and clusters of alpha helices.

It sometimes is possible to determine the shape of a target or portion thereof by crystallography X ray diffraction or by other physical or chemical techniques known to those skilled in the art. Many different computer programs are available for predicting protein secondary and tertiary structure, the most common being those described in Chou & Fasman (Biochemistry, 13:222-245, 1978) and Garnier et al. (J. Mol. Biol., 120:97-120, 1978). Generally, these and other available programs are based on the physical and chemical properties of individual amino acids (hydrophobicity, size, charge, and presence of side chains) and on the amino acids' collective tendency to form identifiable structures in proteins whose secondary structure has been determined. Many programs attempt to weight structural data with their known influences. For example, amino acids such as proline or glycine are often present where polypeptides have share turns. Long stretches of hydrophobic amino acids (as determined by hydropathy plot) usually have a strong affinity for lipids.

Data obtained by the methods described above and other conventional methods and tools can be correlated with the presence of particular sequences of nucleotides in the first and second generation aptamers to engineer second and third generation aptamers. Further, deconvolution of libraries can also be accomplished by sequentially screening from pools of oligonucleotides having more predetermined sequences than the pools used in earlier rounds of selection.

These methods can be used to design optimal binding sequences for any desired target (which can be portions of aptamers or entire aptamers) and/or to engineer into aptamers any number of desired targeted functions or features. Optimal binding sequences will be those which exhibit high relative affinity for target, i.e., affinity measured in $K_d$ in at least in the nanomolar range, and, for certain drug applications, the nanomolar or picomolar range. Studying the binding energies of aptamers using methods known generally in the art can be useful generally, and consensus regions can be identified by comparing the conservation of nucleotides for appreciable enhancement in binding.

Structural knowledge can be used to engineer aptamers. For example, stem structures in the aptamer pool can be vital components where increased structural rigidity is desired. A randomly generated pool of oligonucleotides having the stem sequences can be generated. After aptamers are identified which contain the stem (i.e., use the stem in primers), one can put cross-linkers in the stem to covalently fix the stem in the aptamer structure. Cross-linkers also can be used to fix an aptamer to a target. They can then be used to construct a focused library Once an aptamer has been identified, it can be used, either by linkage to, or use in combination with, other aptamers identified according to these methods. One or more aptamers can be used in this manner to bind to one or more targets.

In order to produce nucleic acids desirable for use as a pharmaceutical, it is preferred that the nucleic acid ligand binds to the target in a manner capable of achieving the desired effect on the target; be as small as possible to obtain the desired effect; be as stable as possible; and be a specific ligand to the chosen target. In most, if not all, situations it is preferred that the nucleic acid ligand has the highest possible affinity to the target. Modifications or derivatizations of the ligand that confer resistance to degradation and clearance in situ during therapy, the capability to cross various tissue or cell membrane barriers, or any other accessory properties that do not significantly interfere with affinity for the target can also be achieved.

Nucleic acid ligands can be derived from the selected aptamers wherein certain chemical modifications are made in order to increase the in vivo stability of the ligand or to enhance or mediate the delivery of the ligand. Examples of such modifications include chemical substitutions at the ribose and/or phosphate positions of a given RNA sequence. See, e.g., WO 9203568; U.S. Pat. No. 5,118,672; Hobbs et al. (Biochem 12:5138-5145, 1973); Guschlbauer et al. (Nucl. Acids Res. 4:1933-1943, 1977); Shibahara et al. (Nucl. Acids. Res. 15:4403-4415,1987); and Pieken et al. (Science 253: 314-317, 1991).

A logical extension of this analysis is a situation in which one or a few nucleotides of the polymeric ligand is used as a site for chemical derivative exploration. The rest of the ligand serves to anchor in place this monomer (or monomers) on which a variety of derivatives are tested for non-interference with binding and for enhanced affinity. Such explorations can result in small molecules that mimic the structure of the initial ligand framework, and have significant and specific affinity for the target independent of that nucleic acid framework. Such derivatized subunits, which can have advantages with respect to mass production, therapeutic routes of administration, delivery, clearance or degradation than the initial ligand, can become the therapeutic and can retain very little of the original ligand. Thus, the aptamers can allow directed chemical exploration of a defined site on the target known to be important for the target function.

Aptamers and derivatives thereof are useful in diagnostic, research and therapeutic contexts. For diagnostic applications, aptamers are particularly well suited for binding to biomolecules that are identical or similar between different species. Classes of molecules such as coagulation factors and transcription factors generally do not serve as good antigens because they are not easily recognized as foreign by the immune systems of animals that can be used to generate antibodies. Antibodies are generally used to bind analytes that are detected or quantitated in various diagnostic assays. Aptamers represent a class of molecules that can be used in place of antibodies for diagnostic and purification purposes.

Aptamers are therefore particularly useful as diagnostic reagents to detect the presence or absence of the targets to which they specifically bind. Such diagnostic tests are conducted by contacting a sample with the specifically binding oligonucleotide to obtain a complex that is then detected by conventional techniques. For example, the aptamers can be labeled using radioactive, fluorescent, or chromogenic labels and the presence of label bound to solid support to which the target has been bound through a specific or non-specific binding means detected. Alternatively, the specifically binding aptamers can be used to effect initial complexation to the support. Techniques for conducting assays using such oligomers as specific binding partners are generally known to track those for standard specific binding partner based assays.

Aptamers can also be used as a separation tool for retrieving the substances to which they specifically bind. By coupling the oligonucleotides containing the specifically binding sequences to a solid support, for example, proteins or other cellular components to which they bind can be recovered in useful quantities. In addition, these oligonucleotides can be used in diagnosis by employing them in specific binding assays for the target. When suitably labeled using detectable moieties such as radioisotopes, the specifically binding oligonucleotides can also be used for in vivo imaging or histological analysis.

The mechanism by which the specifically binding aptamers modulate the biological activity of a target is not always established. They are characterized by their ability to target specific substances and to modulate one or more biological activities regardless of the mechanisms of targeting or the mechanism of the effect thereof.

For use in research, the specifically binding oligonucleotides are especially helpful in effecting the isolation and purification of substances to which they bind. For this application, typically, the oligonucleotide containing the specific binding sequences is conjugated to a solid support and used as an affinity ligand in chromatographic separation of the target. The affinity ligand can also be used to recover previously unknown substances from sources that do not contain the target by virtue of binding similarity between the intended target and the unknown substances. Furthermore, as data accumulate with respect to the nature of the nonoligonucleotide/oligonucleotide-specific binding, insight can be gained as to the mechanisms for control of gene expression.

The aptamers described herein can be used as a separation reagent for retrieving the targets to which they specifically bind. By coupling the oligonucleotides containing the specifically binding sequences to a solid support, for example, the target can be recovered in useful quantities. In addition, these oligonucleotides can be used in diagnosis by employing them in specific binding assays for the target. When suitably labeled using detectable moieties including radioisotopes such as $^{19}F$, $^{99m}Tc$, $^{131}I$, $^{90}Y$, $^{111}In$, $^{123}I$, $^{15}N$, $^{32}P$ or $^{33}P$, the specifically binding oligonucleotides can also be used for in vivo or in vitro diagnosis, imaging or histological analysis by techniques known in the art.

For application in such various uses, the aptamers can be coupled to auxiliary substances that enhance or complement the function of the aptamer. Such auxiliary substances include, for example, labels such as radioisotopes, fluorescent labels, enzyme labels and the like; specific binding reagents such as antibodies, additional aptamer sequence, cell surface receptor ligands, receptors per se and the like; toxins such as diphtheria toxin, tetanus toxin or ricin; drugs such as anti-inflammatory, antibiotic, or metabolic regulator pharmaceuticals, solid supports such as chromatographic or electrophoretic supports, and the like. Suitable techniques for coupling of aptamers to desired auxiliary substances are generally known for a variety of such auxiliary substances, and the specific nature of the coupling procedure will depend on the nature of the auxiliary substance chosen. Coupling can be direct covalent coupling or can involve the use of synthetic linkers such as those marketed by Pierce Chemical (Rockford, Ill.), Thus, the aptamers or derivatives thereof can be used alone in medical treatment or can be used as targeting agents to deliver pharmaceuticals or toxins to desired targets. The aptamers can be used in diagnostic procedures and advantageously in this application include label. They can be used as reagents to separate targets from contaminants in samples containing the targets in which application they are advantageously coupled to solid support.

For example, an aptamer may be synthesized on a solid support column, using techniques such as those described by Beaucage et al. (Tetrahedron Lett. 22:1859-1862, 1981) and Sinha et al. (Nucleosides and Nucleotides 3:157-171, 1984). The final DMT-group is removed from the resulting RNA aptamer. Alternately, if large-scale synthesis is used, the RNA aptamer can be made by scale-up of the solid support method or the RNA aptamer can be made by using solution phase techniques, particularly if the desired end-product is a relatively short oligonucleotide. A starting material for the synthesis process can be a 5'-non-tritylated RNA oligoribonucleotide or analog of the desired primary structure, which preferably can have protected bases, and which is preferably bound to a solid-support. Any conventionally used protecting groups can be used. Typically $N_6$-benzoyl is used for adenine, $N_4$-benzoyl for cytosine, $N_2$-isobutyryl for guanine and $N_2$-benzoyl for 2-aminopurine. Other useful protecting groups include phenoxyacetyl (PAC) and t-butoxyacetyl (TAC). Conveniently, the more base labile protection groups should be used for the synthesis of the RNA or analog fragment, which are known to those of ordinary skill in the art. Such groups can help to prevent hydrolysis of the generated tri- or diphosphates, which are generally quite stable under basic conditions, but could be subject to some hydrolysis. Other envisioned modifications are disclosed in U.S. Pat. No. 6,011,020, incorporated herein by reference, and include but are not limited to the incorporation of bioavailability enhancing molecules such as PEG or cholesterol via a covalent linkage.

A capped RNA or analog can be of any length, the only limit being that of the synthesis technique employed to prepare the RNA or analog. Currently, a preferred length is ranges from approximately 15 to 100 bases, but with improvements in synthetic technology the length of the oligonucleotide is expected to increase. It is preferred that the capped RNA or analog be less than approximately 100 bases in length, and preferably less than about 40 bases in length.

In addition, nucleoside analogs such as 2'-deoxy, 2'-halo, 2'-amino (not substituted or mono- or disubstituted), 2'-mono, di- or trihalomethyl, 2'-O-alkyl, 2'-O-halo-substituted alkyl, 2'-alkyl, azido, phosphorothioate, sulfhydryl, methylphosphonate, fluorescein, rhodamine, pyrene, biotin, xanthine, hypoxanthine, 2,6-diamino purine, 2-hydroxy-6-mercaptopurine and pyrimidine bases substituted at the 6-position with sulfur or 5-position with halo or $C_{1-5}$ alkyl groups, abasic linkers, 3'-deoxy-adenosine as well as other available "chain terminator" or "non-extendible" analogs (at the 3'-end of the RNA), and the like can be incorporated during the RNA synthesis. Further, various labels such as $^{32}P$ or $^{33}P$ and the like can likewise be incorporated during the synthesis, resulting in novel RNA analogs produced by this process. Other envisioned modifications are disclosed in U.S. Pat. No. 6,011,020 and include the incorporation of 3' caps, such an inverted DT cap, or an inverted abasic cap, or combination thereof.

A method of modulating the biological activity of a component or factor in a metabolic or signaling pathway is also provided as another embodiment of the invention. In a preferred embodiment, the method comprises: (a) administering an effective amount of at least one aptamer to a subject (e.g., human or other mammal) in need thereof and (b) modulating a biological activity of the metabolic or signaling pathway in the subject through administering the RNA.

The dosage ranges for the administration of the aptamer depend upon the form of the modulator, and its potency, as described further herein, and are amounts large enough to produce the desired effect in which biological activity is modulated, which can correspondingly ameliorate symptoms of disease or prevent its development. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The individual physician in the event of any complication can also adjust the dosage.

A therapeutically effective amount is an amount of an aptamer sufficient to produce a measurable modulation of the biological activity in the tissue or subject being treated (e.g., a coagulation-modulating amount). By the term "modulate" and grammatical variations thereof, it is intended to promote, inhibit, or otherwise alter one or more biological activities.

An aptamer has the ability to substantially bind to a target in solution at concentrations of less than 1 µM, less than 0.1 µM, or less than 0.01 µM. By "substantially" is meant that at least a 50% reduction in the target's biological activity may be observed by modulation in the presence of the a target, and at 50% reduction is referred to herein as an $EC_{50}$ value.

The aptamer can be administered parenterally by injection or by gradual infusion over time. Although the tissue to be treated can typically be accessed in the body by systemic administration and therefore most often treated by intravenous administration of therapeutic compositions, other tissues and delivery techniques are provided where there is a likelihood that the tissue targeted contains the target. Thus, an aptamer can be administered orally, topically to a vascular tissue, intravenously, intraperitoneally, intramuscularly, subcutaneously, intracavity, transdermally, and can be delivered by peristaltic techniques. Representative, non-limiting approaches for topical administration to a vascular tissue include (1) coating or impregnating a blood vessel tissue with a gel comprising an aptamer for delivery in vivo (e.g., by implanting the coated or impregnated vessel in place of a damaged or diseased vessel tissue segment that was removed or by-passed); (2) delivery via a catheter to a vessel in which delivery is desired; and (3) pumping an aptamer into a vessel that is to be implanted into a patient.

A pharmaceutical composition comprised of an effective amount of at least one aptamer is conventionally administered intravenously, as by injection of a unit dose, for example. The term "unit dose" when used in reference to a pharmaceutical composition refers to physically discrete units suitable as unitary dosage for the subject, each unit containing a predetermined quantity of active material calculated to produce the desired therapeutic effect in association with the required diluent; i.e., vehicle or carrier.

Pharmaceutical compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each subject. But suitable dosage ranges for systemic administration are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

The present invention contemplates pharmaceutical compositions useful for practicing the therapeutic methods described herein. They contain vehicle and optional pharmaceutically-acceptable carrier(s) or excipien(s) together with at least one aptamer as described herein, dissolved or dispersed therein as an active ingredient. In a preferred embodiment, the pharmaceutical composition is not immunogenic when administered to a subject for biological effect or medical treatment (e.g., therapy of existing-disease or prevention of disease).

As used herein, "pharmaceutically acceptable" refers to compositions, carriers, diluents, and reagents and means that such substances are capable of administration to or on a patient for therapy of existing disease or prevention of disease without the production of undesirable physiological effects.

Pharmaceutical compositions comprised of at least one aptamer can be formulated according to known methods such as by the admixture of a vehicle, or pharmaceutically acceptable carrier and excipients. Examples of vehicles, carriers, excipients, and methods of formulation can be found in *Remington's Pharmaceutical Sciences*. To form a pharmaceutical composition suitable for effective administration, such compositions will contain an effective amount of the aptamer. Such compositions can contain admixtures of more than one aptamer. The intended form of administration may guide the form of the composition: e.g., enteric tablets, gel capsules, elixirs, syrup, suppositories, gels, and the like, which is consistent with conventional pharmaceutical practices.

For instance, for oral administration in the form of a tablet or capsule, the aptamers or their derivatives can be formulated with a nontoxic pharmaceutically acceptable oral carrier such as ethanol, glycerol, saline, water, and the like. When desired or necessary, suitable binders, lubricants, disintegrating agents, and coloring agents can also be incorporated into the mixture. Suitable binders include without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes, and the like. Lubricants used in these dosage forms include, without limitation, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

For liquid forms, the aptamers or their derivatives can be formulated in flavored suspending or dispersing agents such as the synthetic and natural gums, for example, tragacanth, acacia, methyl cellulose, and the like. Other dispersing agents that can be employed include glycerin and the like. For parenteral administration, sterile suspensions, and solutions are desired. Isotonic preparations that generally contain suitable preservatives are employed when intravenous administration is desired.

Topical preparations containing aptamers or their derivatives can be admixed with a variety of carrier materials well known in the art, such as, e.g., alcohols, aloe vera gel, allantoin, glycerine, vitamin A and E oils, mineral oil, PPG2 myristyl propionate, and the like to form, e.g., alcoholic solutions, topical cleansers, cleansing creams, skin gels, skin lotions, and shampoos in cream or gel formulations.

Aptamers or their derivatives can also be administered through liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Aptamers or their derivatives can also be coupled with soluble polymers as targetable drug carriers. Such polymers can include polyvinylpyrrolidone, pyran copolymer, polyhydroxypropylmethacryl-amidephenol, polyhydroxyethylaspartamidephenol, or polyethyleneoxidepolylysine substituted with palmitoyl residues. Furthermore, they can be coupled (preferably via a covalent linkage) to a class of biodegradable polymers useful in achieving controlled release of a drug, for example, polyethylene glycol (PEG), polylactic acid, polyepsilon caprolactone, polyhydroxy butyric acid, polyorthoesters, polyacetals, polydihydropyrans, polycyanoacrylates, and cross-linked or amphipathic block copolymers of hydrogels. Cholesterol and similar molecules can be linked to the aptamers to increase and prolong bioavailability.

Therapeutic or prophylactic compositions are administered to a subject in an amount sufficient to provide therapy for existing disease or prevent disease. The effective amount can vary according to a variety of factors such as the individual's condition, weight, sex, and age. Other factors include the mode of administration. Generally, the compositions will be administered in dosages adjusted for body weight (e.g., dosages ranging from about 1 μg/kg body weight to about 1 mg/kg body weight).

As noted above, the pharmaceutical compositions can be provided to the individual by a variety of routes such orally, topically to a vascular tissue, intravenously, intraperitoneally, intramuscularly, subcutaneously, intracavity, transdermally, and can be delivered by peristaltic techniques. Representative, non-limiting approaches for topical administration to a vascular tissue include (1) coating or impregnating a blood vessel tissue with a gel comprising an aptamer for delivery in vivo (e.g., by implanting the coated or impregnated vessel in place of a damaged or diseased vessel tissue segment that was removed or by-passed); (2) delivery via a catheter to a vessel in which delivery is desired; and (3) pumping an aptamer composition into a vessel that is to be implanted into a patient. Alternatively, the aptamer can be introduced into cells by microinjection, or by liposome encapsulation. Advantageously, aptamers can be administered in a single daily dose, or the total daily dosage can be administered in several divided doses.

The dosage regimen utilizing the aptamers is selected in accordance with a variety of factors including type, species, age, weight, sex, and medical condition of the subject; the severity of the condition to be treated; the route of administration; the renal and hepatic function of the subject; and the particular aptamer employed. A physician of ordinary skill can readily determine and prescribe the effective amount of the aptamer required to prevent progress of the condition. Optimal precision in achieving concentrations of aptamer within the range that yields efficacy without toxicity requires a regimen based on the kinetics of the aptamer's availability to target sites. This involves a consideration of the distribution, equilibrium, and elimination of the aptamer in the body.

A method of isolating one or more aptamers by their specifically binding to a target from a candidate mixture of potential ligands comprises (a) preparing a candidate mixture of potential ligands; (b) contacting the candidate mixture with a target under binding conditions, wherein ligands having increased affinity to the target relative to the candidate mixture bind to the target; (c) removing unbound fraction of the candidate mixture; (d) collecting ligands that are bound to the target; and (e) amplifying the ligands able to bind to the target. Optionally, these steps are repeated as necessary to select a desired ligand.

In an alternative embodiment, the method comprises: (a) immobilizing a target on a substrate; (b) preparing a candidate mixture of potential ligands; (c) passing the candidate mixture over the substrate under binding conditions, wherein ligands having increased affinity to the immobilized target relative to the candidate mixture bind to the immobilized target; (d) passing a wash buffer over the substrate to remove unbound candidate mixture; (e) passing an eluting buffer over the substrate to elute ligands that are bound to the immobilized target to produce an eluted ligand mixture; and (f) amplifying the ligands able to bind to the immobilized target. Optionally, these steps are repeated as necessary to produce as desired ligand.

The method is applicable to any target as defined herein for which a ligand is sought. In a preferred embodiment, the method further comprises amplifying the eluted ligand to yield a ligand-enriched mixture, whereby a ligand to the target is identified. The ligand mixture can comprise a candidate mixture of any ligand as defined herein, including but not limited to nucleic acids. In this case, the candidate mixture of nucleic acids comprises single strand nucleic acids. The single stranded nucleic acids can comprise deoxyribonucleic acids.

Preferably, the single stranded nucleic acids are ribonucleic acids. In this case amplification can be accomplished, for example, via reverse transcriptase PCR reactions as described in U.S. Pat. No. 5,817,785. Optionally, the candidate mixture of nucleic acids can comprise 2'-modified ribonucleic acids. For example, the 2'-modified ribonucleic acids can comprise 2'-fluoro modified nucleic acids.

Representative wash and elution buffers are described in U.S. Pat. Nos. 5,475,096 and 5,861,254. For example, after nucleic acids are incubated with target, the nucleic acid/protein mixture may be filtered through a nitrocellulose filter and washed with appropriate buffer to remove free nucleic acids. Protein/nucleic acids often remain bound to the filter. Filter washing procedure can be optimized to reduce background binding. Such optimization of the filter washing procedures is within the skill of the ordinary artisan.

Any suitable eluting buffer as would be apparent to one of ordinary skill in the art can also be employed. For example, with respect to nucleic acid ligands, in order to proceed to the amplification step, selected nucleic acids must be released from the target after partitioning. This process is preferably done without chemical degradation of the selected nucleic acids and preferably results in amplifiable nucleic acids. For example, selected RNA molecules can be eluted from nitrocellulose filters using a freshly made solution containing 200 μl of 7 M urea, 20 mM sodium citrate (pH 5.0), 1 mM EDTA solution combined with 500 μl of phenol (equilibrated with 0.1 M sodium acetate pH 5.2). A solution of 200 μl of 7 M urea with 500 μl of phenol can also be employed. In this case, the eluted solution of selected RNA can then be extracted with ether, ethanol precipitated, and the precipitate re-suspended in water. A number of different buffer conditions for elution of selected RNA from the filters can be used. For example, without limitation non-detergent aqueous protein denaturing agents such as guanidinium chloride, guanidinium thiocyanate, etc. as are known in the art can be used. The specific solution used for elution of nucleic acids from the filter can be routinely selected by one of ordinary skill in the art.

As is understood in the art, the concentration of various ions (in particular, the ionic strength) and the pH impact on the value of the dissociation constant of the target/ligand complex. Thus, the terms "lower stringency" and "higher stringency" pertain to such buffer conditions (e.g., binding buffer conditions) as salt concentration, ionic strength generally, pH, temperature, or organic solvents, as will be readily appreciated by those skilled in the art after review of the disclosure presented herein.

The method can further comprise repeating washing and/or eluting steps in a higher stringency buffer. Optionally, the higher stringency buffer comprises a physiological buffer. As used herein, "physiological conditions" means the salt concentration and ionic strength in an aqueous solution that characterize fluids found in human metabolism commonly referred to as physiological buffer or physiological saline. In general, these are represented by an intracellular pH of about 7.1 and salt concentrations (in mM) of $Na^+$: 3-15; $K^+$: 140; $Mg^{+2}$: 6.3; $Ca^{+2}$: 10-14; $Cl^-$: 3-15, and an extracellular pH of 7.4 and salt concentrations (in mM) of $Na^+$: 145; $K^+$: 3; $Mg^{+2}$: 1-2; $Ca^{+2}$: 1-2; and $Cl^-$: 110. The use of physiological conditions in the ligand selection method is important, particularly with respect to those ligands that can be intended for therapeutic use.

SELEX is a powerful iterative affinity purification process that can be employed to isolate rare ligands from nucleic-acid combinatorial libraries. As such, it is necessary to establish conditions under which the desired biological activity can be detected in the initial randomized library prior to initiating the SELEX process. In addition, to purify ligands possessing this activity from other sequences within the randomized pool, the signal of the desired activity must be above the "noise" of library binding to the partitioning scheme (i.e., the fraction of sequences binding to the partitioning media due to target binding must be greater than those binding in a target independent manner).

Generally, the SELEX process can be defined by the following series of steps:

(1) A candidate mixture of nucleic acids having different sequences is prepared. The candidate mixture generally includes regions of fixed sequences (i.e., each of the members of the mixture contains the same sequences in the same location) and regions of randomized sequences. The fixed sequence regions are selected either: (a) to assist in the amplification steps described below; (b) to facilitate mimicry of a sequence known to bind to the target; or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

(2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and the nucleic acids having the strongest affinity for the target.

(3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5-50%) are retained during partitioning.

(4) Those nucleic acids selected during partitioning as having the relatively higher affinity to the target are then amplified to create a new candidate mixture that is enriched in nucleic acids having a relatively higher affinity for the target.

(5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target.

The desired characteristics for a given nucleic acid ligand can vary. All nucleic acid ligands are capable of forming a complex with the target. In some cases, it is desired that the nucleic acid ligand will serve to inhibit one or more of the biological activities of the target. In other cases, it is desired that the nucleic acid ligand serves to modify one or more of the biological activities of the target. In other cases, the nucleic acid ligand serves to identify the presence of the target, and its effect on the biological activity of the target is irrelevant.

In order to identify conditions that are preferred for the initiation of the SELEX process (i.e., signal to noise ratio greater than 2), a matrix strategy to evaluate target dependent versus target independent binding of the library under different conditions is provided. While this strategy is employed to identify SELEX conditions that are physiologic or that approach physiologic for the target, it could readily be applied to identify very non-physiologic conditions if one desired to use an aptamer in downstream processes that require solvents that are non-physiologic.

The monovalent salt concentration and pH of the binding buffer are varied in combination to evaluate monovalent salt concentrations of about 25 mM, 50 mM, 75 mM, 100 mM, 125 mM, or 150 mM (e.g., from 25 mM to 150 mM or any interval thereof) and a pH range of about 6.5, 7.0, 7.5, or 8.0 (e.g., from pH 6.5 to 8.0 or any interval thereof) in binding reactions with radiolabeled randomized library RNA and varying concentrations of target. All binding buffers also contain physiologic concentrations of the appropriate divalent metal ions (depends on the in vivo compartment of the target) and excipient as needed to maintain the protein in solution in a native state. This systematic variation of these critical parameters allows for the rapid identification of the buffer conditions and target concentration under which the SELEX process can be successfully initiated. In some cases, the initial conditions are non-physiologic with respect to the monovalent salt concentration, the pH, or both. In these cases, the matrix strategy can be employed again in subsequent rounds of the SELEX process to determine when the conditions (i.e., binding buffer) of the SELEX can be changed. This strategy is repeated every few rounds until the SELEX process can be continued under physiologic conditions.

EXAMPLE 1

Focused Library Constructed Against the Platelet Proteome

Figure 5:
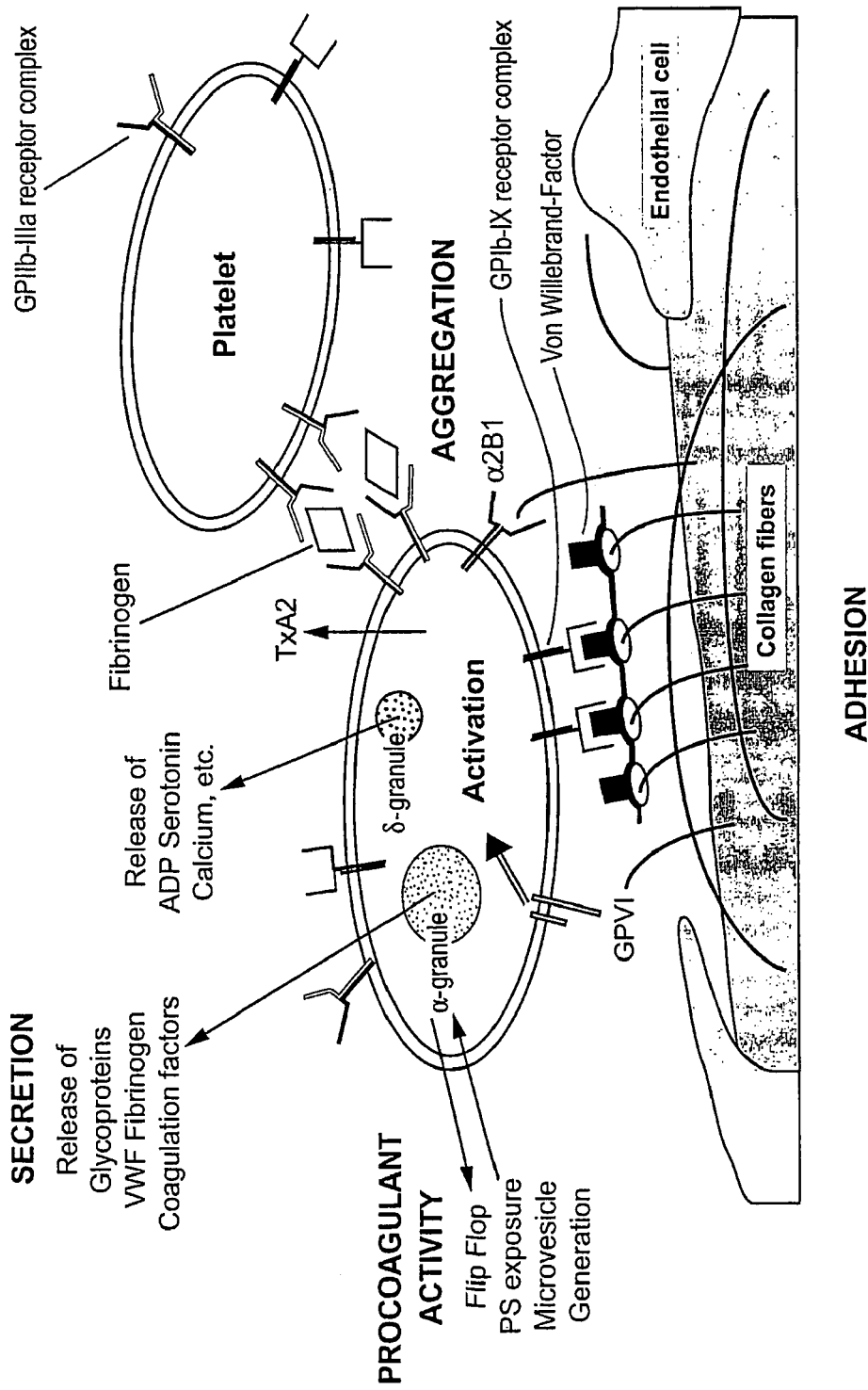
FIG. 5 illustrates the role of platelets in hemostasis as shown in Harrison (Blood Rev. 19:111-123, 2005).

Platelets play an important role in hemostasis and the pathogenesis of arterial thrombosis (FIG. 5). When blood vessels are damaged, the small anucleated cell fragments adhere to the exposed subendothelium, are activated, aggregate with one another, and start thrombin generation. Ultimately a platelet plug, which is stabilized by the conversion of fibrinogen to fibrin by thrombin, is formed that stems blood loss at the site of injury. To fulfill their fundamental role in hemostasis, platelets rely on a multitude of surface receptors, as well as other proteins, which are current targets for anti-platelet drug development.

Figure 6:
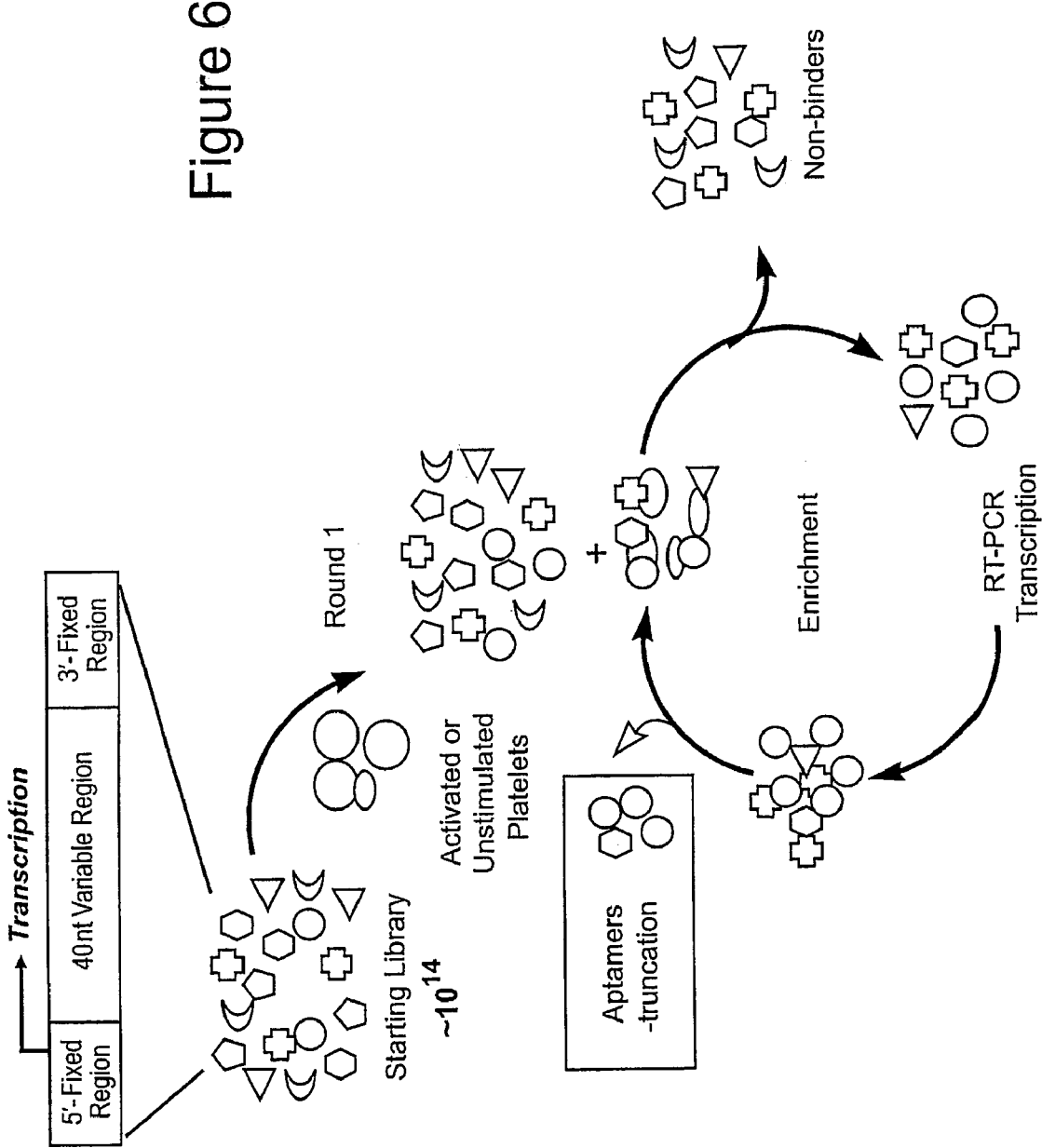
FIG. 6 illustrates a schematic for construction of the focused library against a platelet proteome. Transcription of the cassette provide RNA ligand for the library. The variable region provides sequence diversity, the 5'- and 3'-fixed regions allow amplification by primer binding to those regions, and the promoter transcribes RNA for single stranded nucleic acid. Here, the initial collection was randomized during solid-phase chemical synthesis of the variable region.
Figures 7A, 7B:
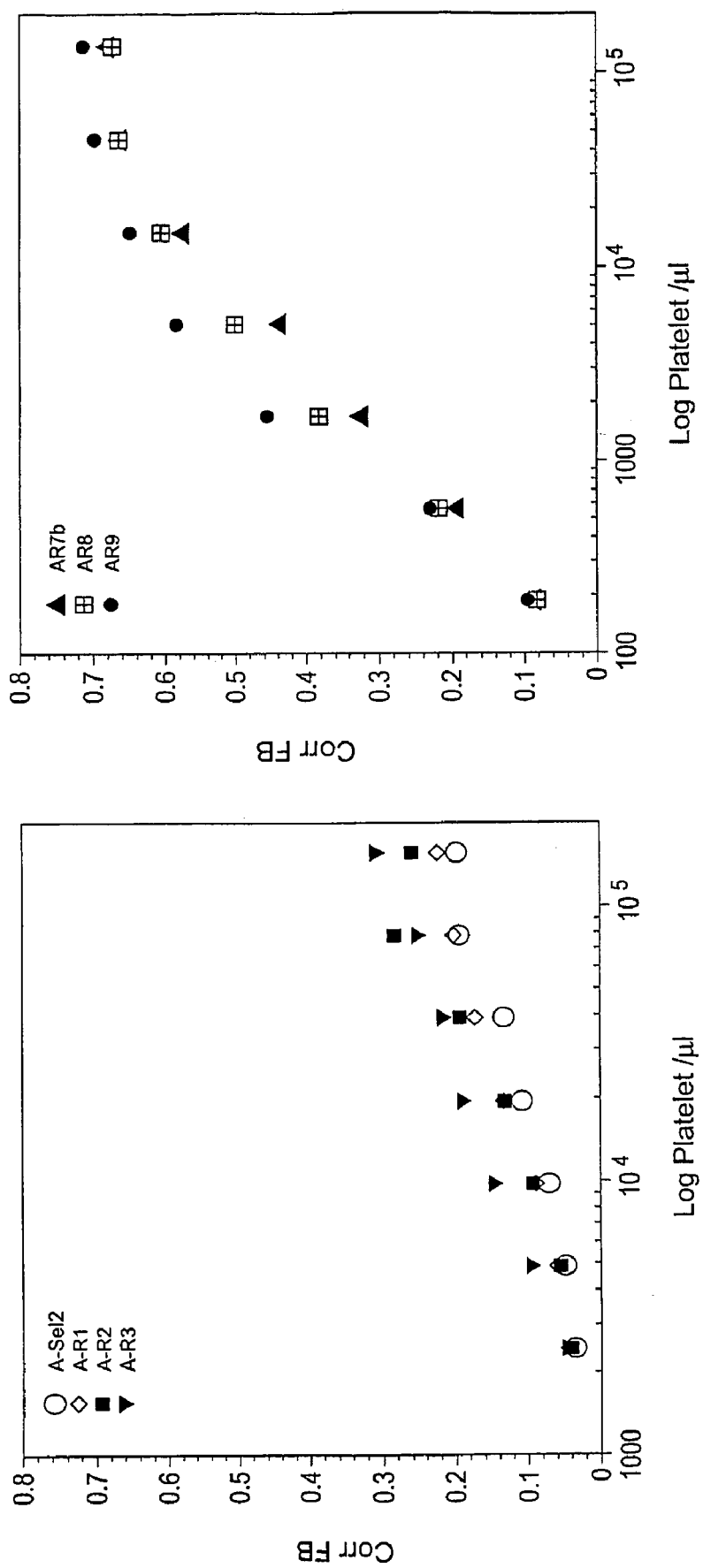
FIG. 7A shows the binding curve of activated platelets incubated with Sel2 library and Rounds 1 to 3.
FIG. 7B shows Rounds 7 to 9.
Figure 7C:
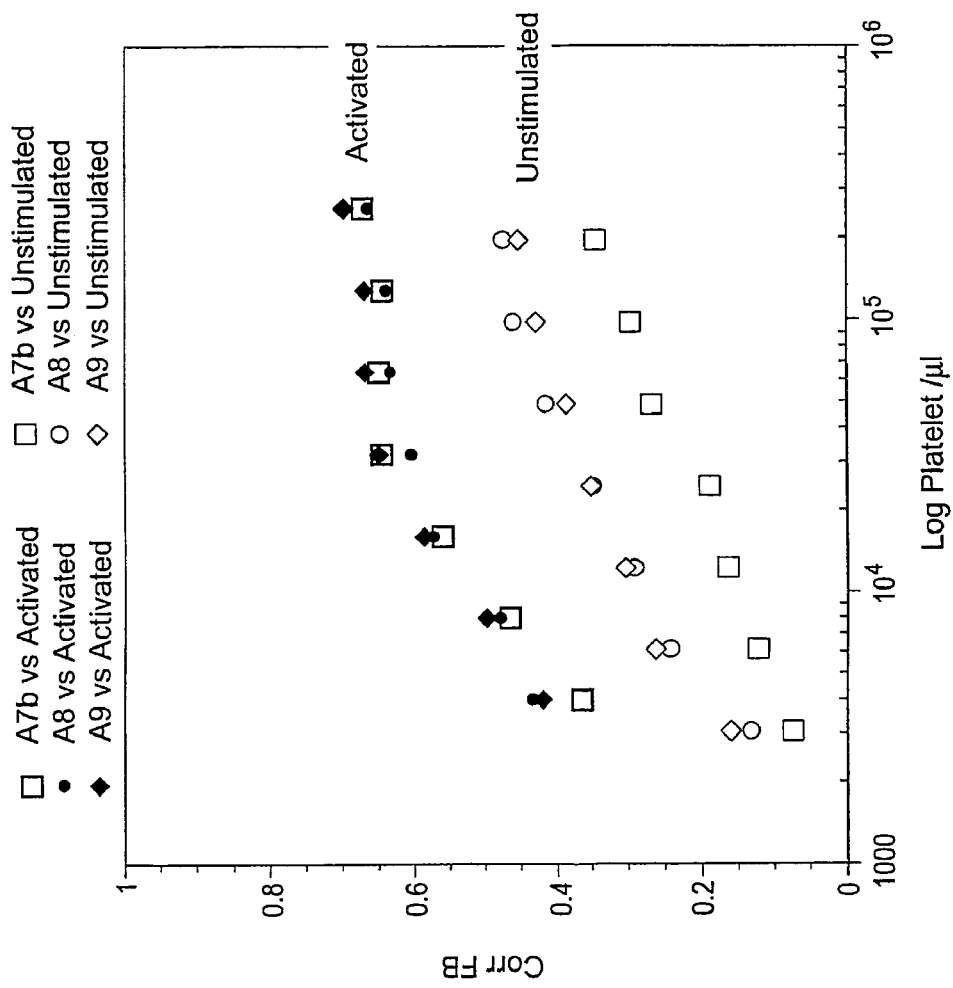
FIG. 7C shows RNA pools after focusing against the proteome of activated platelets (Rounds 7 to 9), which displayed different binding curves when incubated against the proteome of unstimulated platelets.
Figure 10:
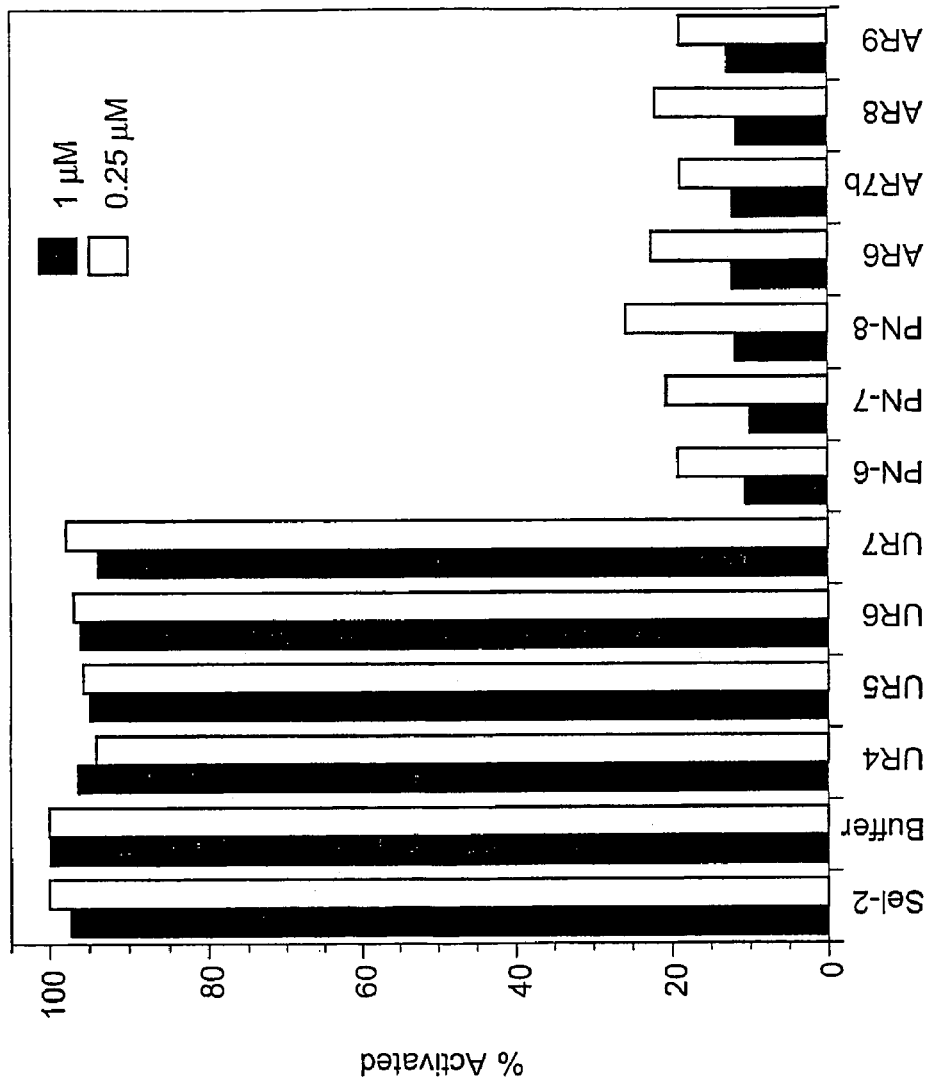
FIG. 10 shows another functional assay where there are RNA pools which contain at least one aptamer that was biologically active. Platelet activation was modulated in a CD62P activation assay. This is another example of deconvoluting the focused library into pools in accordance with functional profiling.
Figure 11:
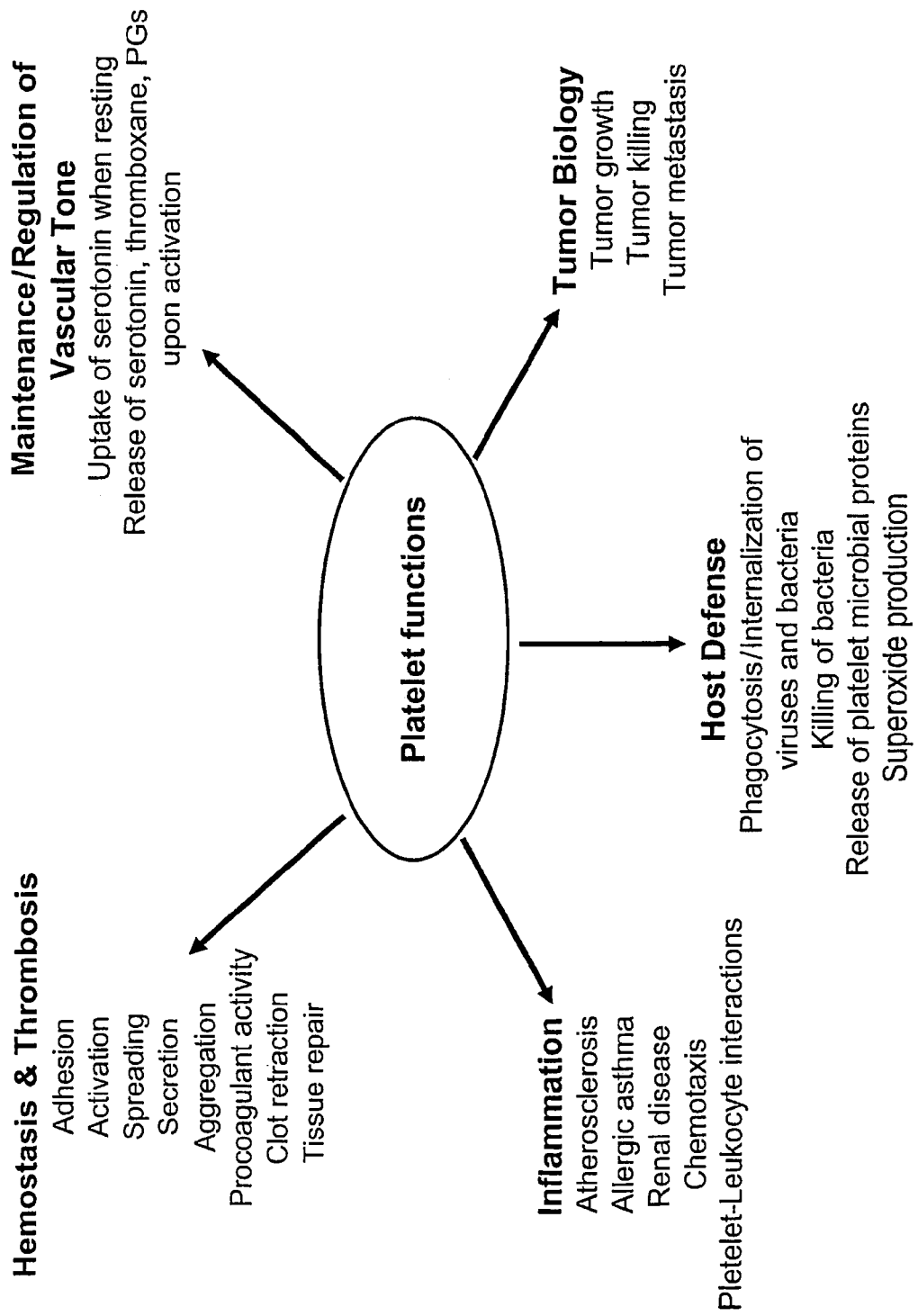
FIG. 11 illustrates platelet function as shown in Harrison (Blood Rev. 19:111-123, 2005).

We constructed a focused library of aptamers against the proteome of purified platelets. Negative selection against a complex mixture of native proteins (i.e., a first proteome) of unstimulated platelets was also performed before positively selecting against a complex mixture of native proteins (i.e., a second proteome) of activated platelets. After several rounds of selection, we were able to generate a more limited RNA library that is now focused on the platelet proteome. See FIGS. 6-8. A series of functional and platelet adhesive assays are now being used to characterize these aptamers and their specific targets (see FIGS. 9-10). A focused library specific for platelet targets may hold great potential in the fields of anti-platelet drug development as well as in diagnostics where aptamer are able to modulate platelet function (FIG. 11).

Figures 8, 9:
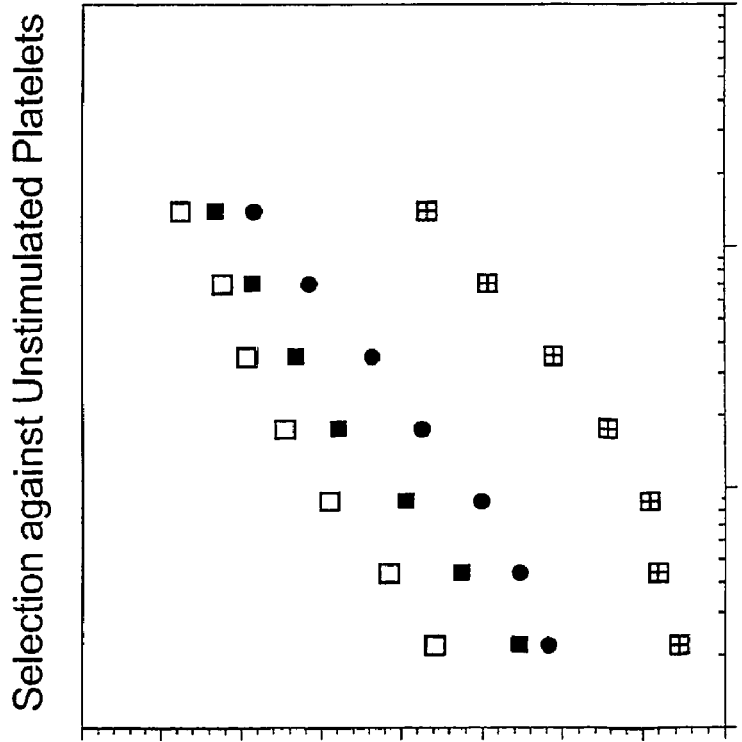
FIG. 8 shows selection against the proteome of unstimulated platelets.
FIG. 9 shows RNA pools which contain at least one aptamer that was biologically active in a functional assay. Platelet function in a PFA assay was modulated. This is also an example of deconvoluting the focused library into pools in accordance with functional profiling.

By using an iterative process of selecting for high binding affinity nucleic acids, we obtained a focused library against the proteome of fibrin-activated platelets. The library contains aptamers with anti-platelet biological activities as shown in FIGS. 9-1-. Anti-platelet aptamers are attractive alternative to existing drugs because their effects can be easily reversed with antidotes (Rusconi et al., Nature Biotechnol. 22:1423-1428, 2004).

EXAMPLE 2

Focused Library Constructed Against the Plasma Proteome

Figure 12:
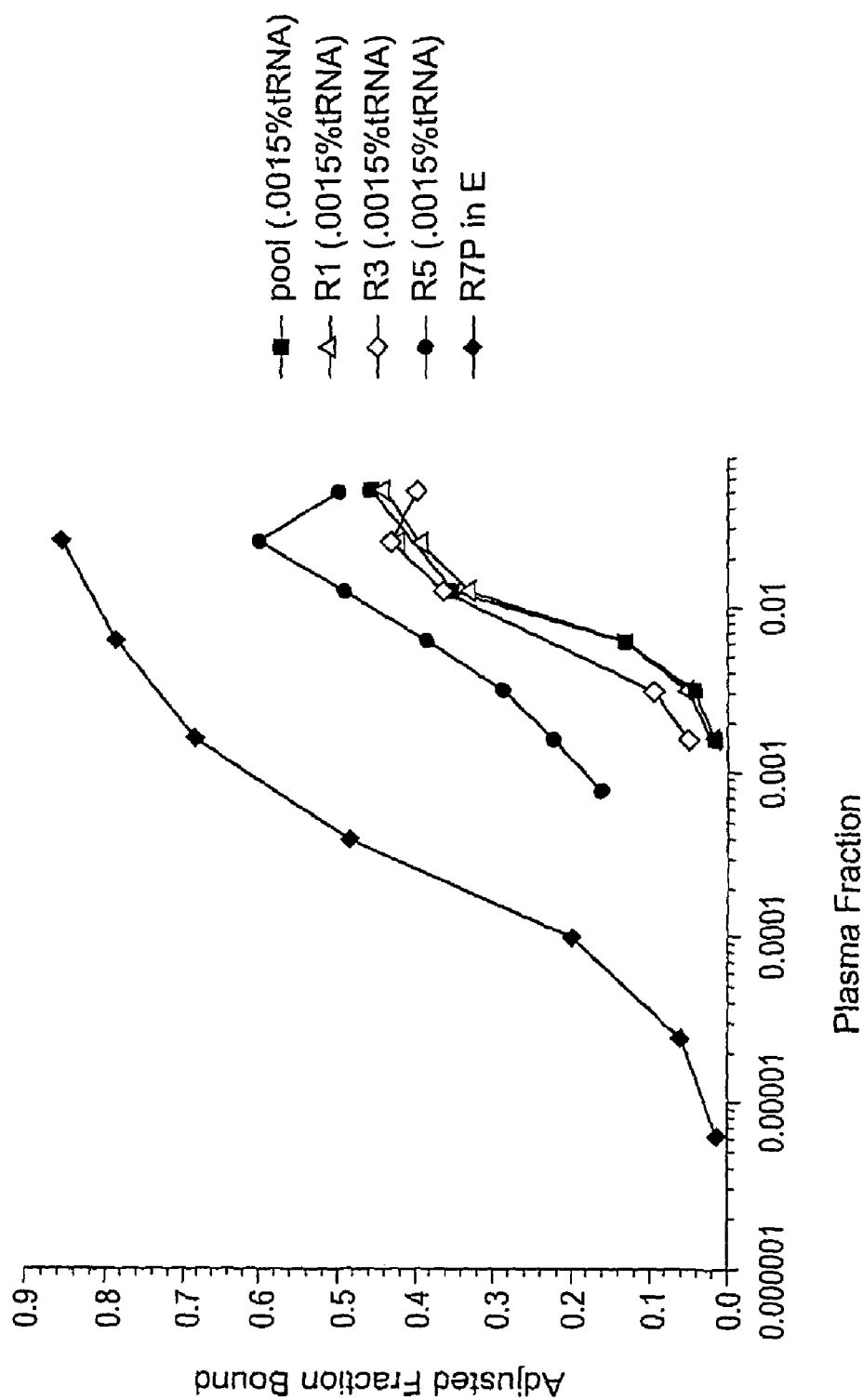
FIG. 12 shows that focused libraries (R5 and R7P) bind plasma proteins with increased affinity in comparison with a random pool of nucleic acids (i.e., unfocused library).

We constructed a focused library of aptamers against the proteome of human plasma. Here, the nucleic acids are modified RNA and the targets are proteins. The aptamers isolated from the focused library are directed against von Willebrand Factor (VWF) and the Fc portion of human immunoglobulin IgG. Over successive rounds, the focused libraries (R5 and R7P) bind proteins of the plasma proteome with greater affinity than an initial pool of RNA aptamers having random sequences (FIG. 12).

EXAMPLE 3

Focused Library Constructed Against GLA-Containing Proteins

Figure 13:
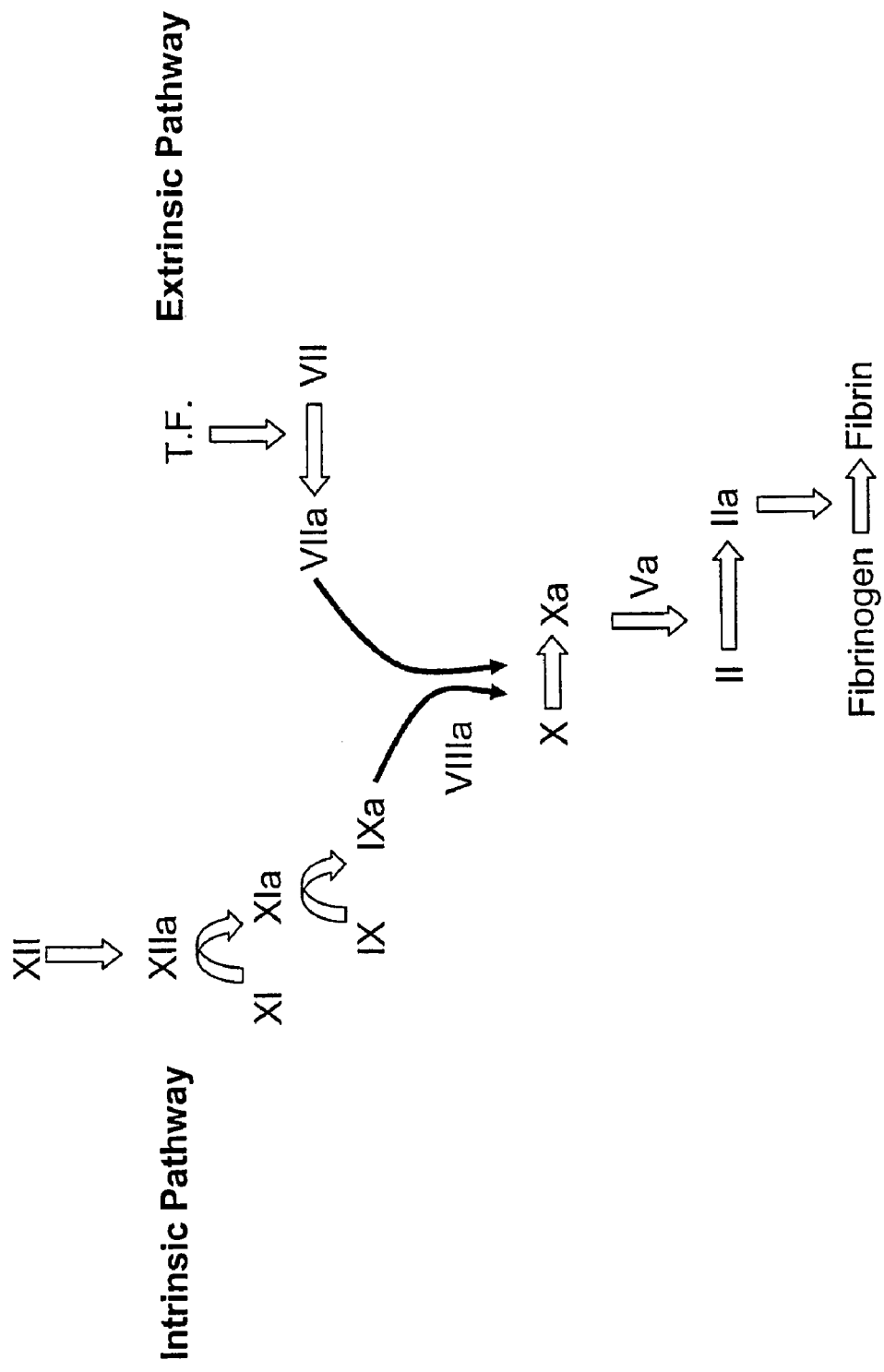
FIG. 13 illustrates the coagulation cascade with the following GLA proteins: Factor II, Factor VII, Factor IX, and Factor X.

The blood coagulation pathways consists of a series of enzymatic reactions that ultimately results in thrombin converting fibrinogen into a fibrin clot (FIG. 13). A subset of coagulation proteins is the vitamin K-dependent GLA serine protease zymogens, which are characterized by the presence of a gamma-carboxyglutamic acid domain (GLA) at the amino end of the proteins. The GLA proteins are Factor II, Factor VII, Factor IX, Factor X, Protein C, Protein S, and Protein Z. Even though the target proteins are present in the proteome at concentrations that differ by up to 100-fold, aptamers were isolated which bind the different targets.

Figure 14:
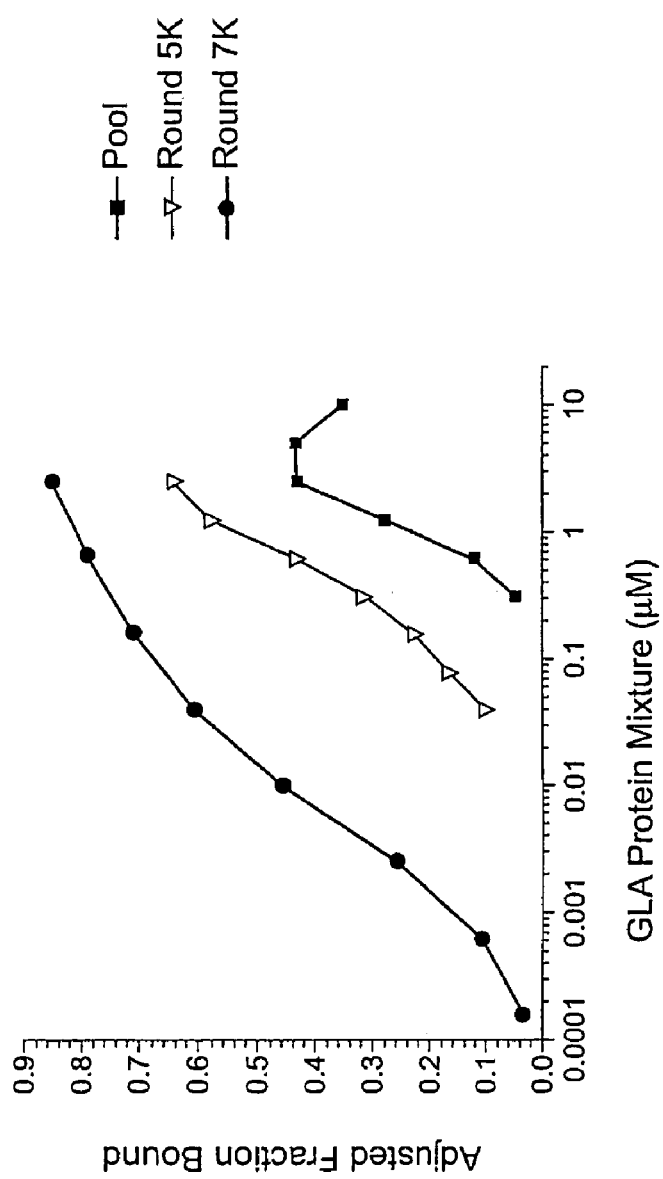
FIG. 14 shows the selection of aptamers binding to GLA proteins and clones of interest from Round 7.

By using SELEX against the complex mixture containing GLA proteins, we isolated aptamers to Factor II and Factor X from that focused library (FIG. 14). The aptamers have very high binding affinities and anticoagulate human plasma.

Figure 15:
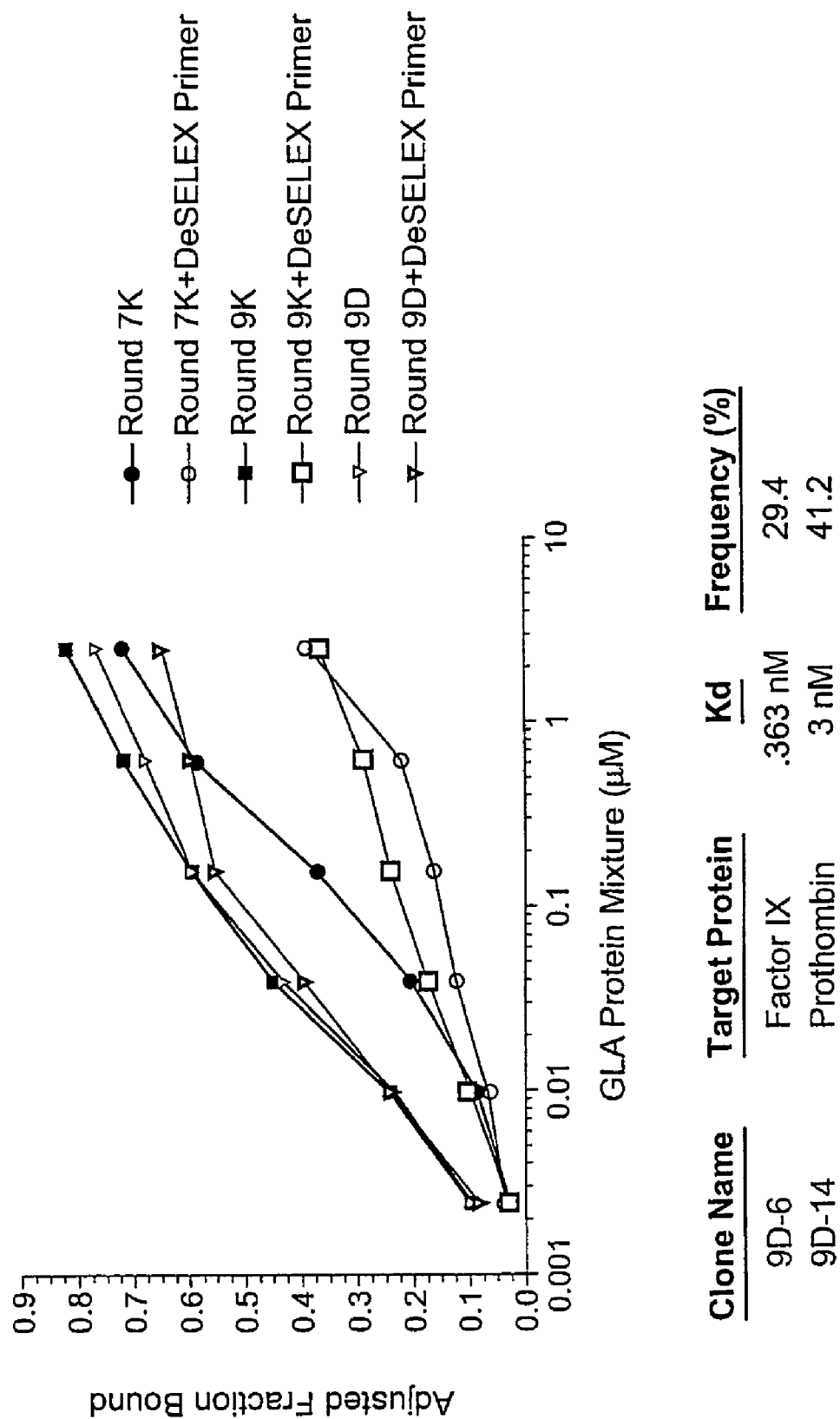
FIG. 15 shows binding curves after DeSELEX demonstrating depletion of dominant clone 7K-3 from a focused library and selection of aptamers binding to other targets.

With any selection of nucleic acids and their amplification over several rounds, a particular sequence can come to dominate. By "deselecting" the dominant aptamer, isolating of further candidate aptamers can be redirected towards other sequences. By using DeSELEX, we were able to shift the selection towards other scarcer sequences in the focused library and targets in the proteome. An oligonucleotide complementary to the random region of clone 7K-3 was designed. By annealing the DeSELEX oligo to the focused library, the sequence of clone 7K-3 was prevented from binding to its target. Such sequences were depleted from the library during subsequent partitioning and amplifying of nucleic acids. Here, further selection of nucleic acids from later libraries was redirected to less abundant aptamers and their more scarce targets in the proteome. An anticoagulant aptamer to Factor IX was isolated (FIG. 15).

Figure 16:
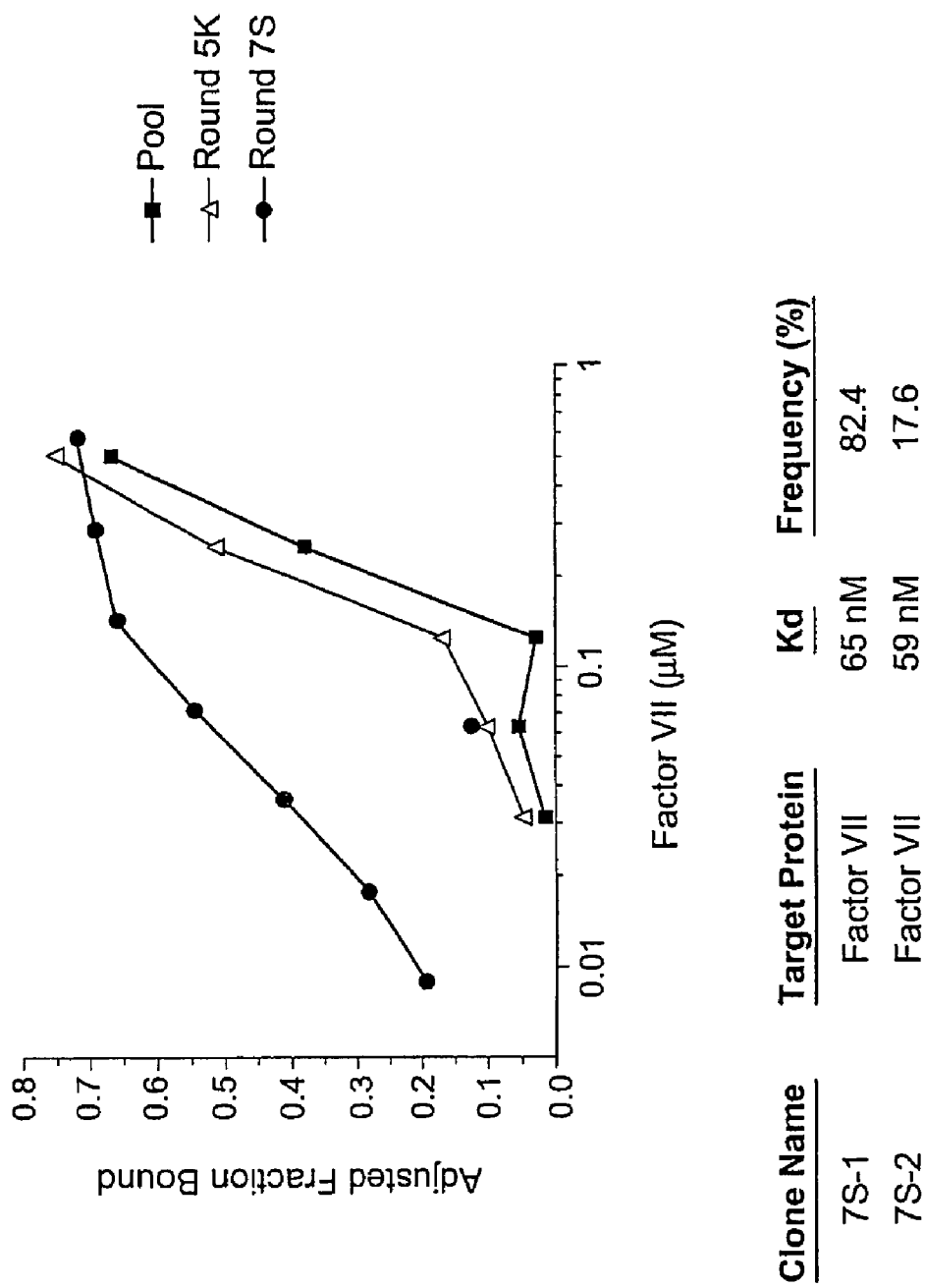
FIG. 16 shows two rounds of Laser SELEX against Factor VII resulted in the isolation of two clones.

We also demonstrated that by using Laser SELEX, selection of nucleic acids in a focused library could be efficiently and rapidly directed to candidate aptamers which bind to another target in the proteome. Clones were isolated by specific binding to Factor VII (FIG. 16), Factor, II, Factor X, and Factor IX.

Figure 17:
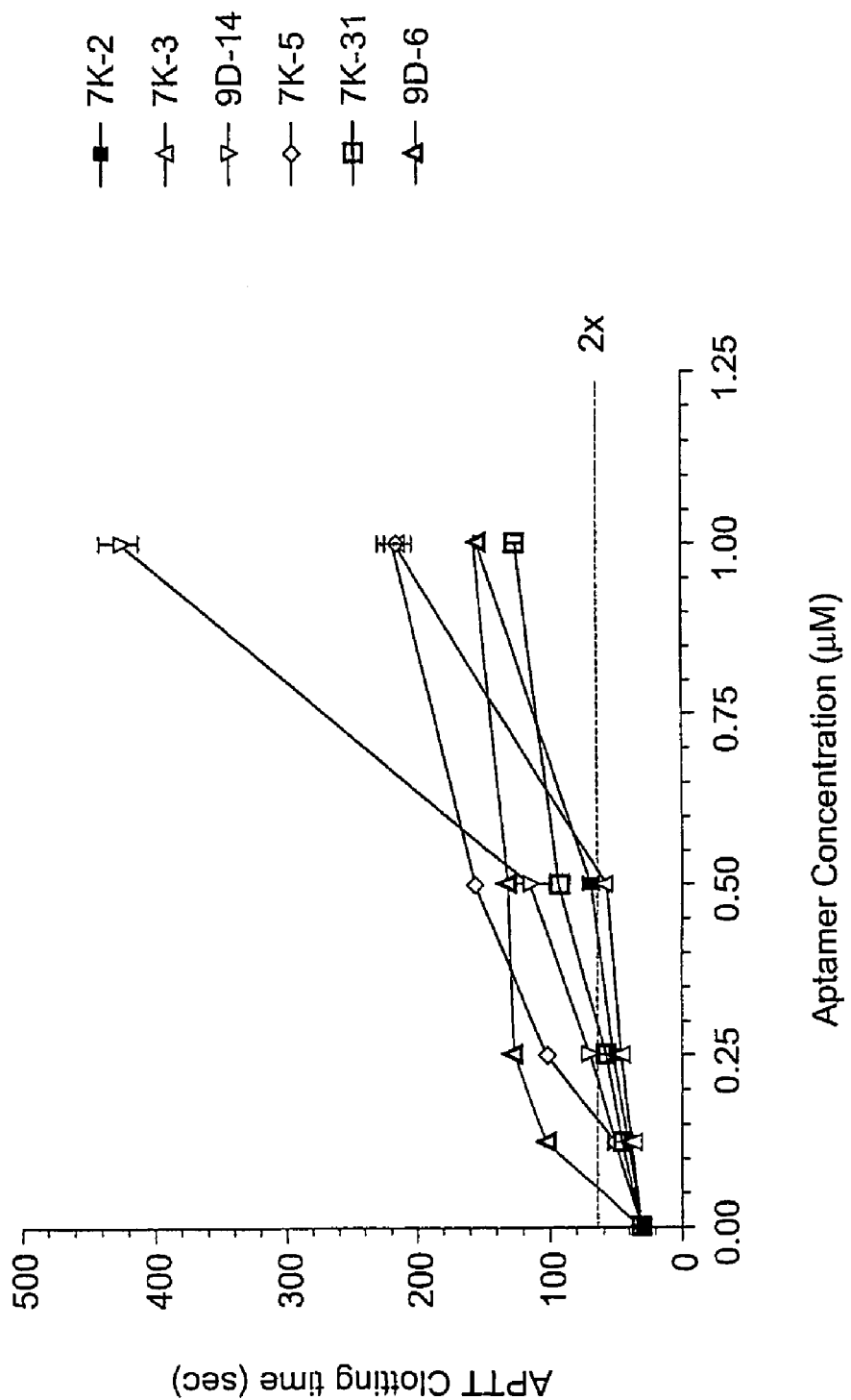
FIG. 17 shows activated partial thromboplastin time (APTT) clotting data demonstrating that aptamers are functional as anticoagulants. Clotting assays are an example of a functional assay used to determine whether a candidate aptamer can modulate biological activity.

Aptamers were isolated against the GLA-containing family of proteins: Factor II (prothrombin), Factor VII, Factor IX, and Factor X. Factor II aptamers were functionally assayed and are anticoagulants (FIG. 17). The aptamers are comprised of the variable regions listed in the attached Sequence Listing, but they may be substituted with functional equivalents that are derivatives thereof (e.g., one or more bases replaced with ribonucleotide analogs, one or more phosphodiesters replaced with modified base linkages, which may be used to inhibit the indicated biological activities). The partial sequences of the aptamers are shown in the Sequence Listing: Factor VII (nucleotide sequences of their random regions are SEQ ID NOS:1-11), Factor II (nucleotide sequences of their random regions are SEQ ID NOS:12-27), Factor X (nucleotide sequences of their random regions are SEQ ID NOS: 28-43), and Factor IX (nucleotide sequences of their random regions are SEQ ID NOS:44-49). Also poor binders and contaminants having unknown binding activity were isolated: nucleotide sequences of their random regions are SEQ ID NOS:50-65, which may be used as controls to establish minimal binding constants $K_d$ and $B_{max}$ (e.g., 7K-85, 9K-5, 9K-8, 10S-4, 10S-5, 10S-6, 10S-9, 10S-12 and 10S-16 are poor binders of Factor X; 7K-48 and 10S-6 have insignificant APTT activity; 7K-6, 7K-8, 7K-19, 7K-116 and 7K-128 have poor APTT activity; 7K-55 has fair APTT activity; 10S-9 and 10S-12 have little PT activity and significant APTT activity). Binding parameters of some functional aptamers are shown in Table 1.

TABLE 1

Binding and Functional Data of Selected Clones

| Clone | Binding Activity | Functional Activity | $K_d$ (nM) | $B_{max}$ |
|---|---|---|---|---|
| 17-1 | Factor VII/VIIa | Factor VII/VIIa | 53/45 | 0.71/0.76 |
| 17-7 | | Factor VIIa | 70 | 0.78 |
| 17-12 | | Factor VIIa | 70 | 1.1 |
| 7S-2 | | Factor VII | 56 | 0.59 |
| 7K-2 | Factor II/IIa | Factor II/IIa | 36/6 | 0.53/0.86 |
| 7K-3 | | Factor II/IIa | 11/3 | 0.63/0.79 |
| 9D-14 | | Factor II/IIa | 1/1 | 0.71/0.77 |
| 7K-84 | | Factor IIa | 84 | 0.80 |
| 9D-11 | | Factor IIa (poor) | 0.13 | 0.80 |
| 7K-58 | | Factor II | 67 | 0.64 |
| 7K-5 | Factor X/Xa | Factor X/Xa | 12/4 | 0.67/0.69 |
| 9D-24 | | Factor X/Xa | 36/15 | 0.58/0.68 |
| 10S-20 | | Factor X/Xa | 9/7 | 0.81/0.82 |
| 10S-10 | | Factor X/Xa | 41/40 | 0.47/0.50 |
| 10S-19 | | Factor X/Xa | 27/26 | 0.40/0.39 |
| 10S-13 | | Factor X/Xa | 77/51 | 0.79/0.77 |
| 9D-26 | | Factor X | >500 | no plateau |

The activity of 17-1 is typical of clones comprising SEQ ID NOS:1-7. The activity of 7S-2 is typical of clones comprising SEQ ID NOS:10-11; it does not anticoagulate mouse, pig, dog, or rabbit blood (i.e., 7S-2 is specific for human).

Clones 7K-2 and 7K-3 do not compete with Tog 25 for binding to Factor II/IIa (prothrombin/thrombin). The activity of 7K-3 is typical of clones comprising SEQ ID NOS:13-15. The activity of 7K-84 is typical of clones comprising SEQ ID NOS:22-24. Clone 7K-84 can also bind Factor VII; it has no detectable PT activity and little APTT activity. Clone 9D-11 binds Factor II minimally. The activity of 7K-58 is typical of clones comprising SEQ ID NOS:26-27. Clone 7K-58 can also bind Factor VII.

The activity of 7K-5 is typical of clones comprising SEQ ID NOS:28-31. The activity of 9D-24 is typical of clones comprising SEQ ID NOS:32-34. The activity of 10S-20 is typical of clones comprising SEQ ID NOS:35-36. The activity of 10S-10 is typical of clones comprising SEQ ID NOS: 37-40. Clones 10S-10 and 10S-19 had no detectable PT activity. Clone 1.0S-13 has no detectable PT activity and minimal APTT activity.

Clones 9D-6, 9D-10, 9D-15, 9D-20 and 9D-31 bind Factors IX and IXa; the former inhibits with a subnanomolar $K_d$ and $B_{max}$ of greater than 0.9. Clone 7K-41 binds Factor IX poorly but is a better binder of Factor IXa (no binding to Factor XI or Factor XII was detected); it has good anticoagulant activity.

EXAMPLE 4

Binding to von Willebrand Factor and Inhibiting Biological Activity

RNA aptamers containing 2'-fluoro modified pyrimidines and 5-hydroxyl modified purines were isolated by their binding and inhibiting VWF activity in platelet activity assays. The following sequences from the "random" region of the isolated clones are shown.

```
Clone FM10:
                                         (SEQ ID NO: 66)
AUCGCGCUCUCCUGCUUAAGCAGCUAUCAAAUAGCCCACU Clone Q_W3-6:
                                         (SEQ ID NO: 67)
ACCGCGCUCUCCUGCUUAAGCAGCUAUCAAAUAGCCCA-CU Clone Q-W1-9:
                                         (SEQ ID NO: 68)
AUCGCGCUCUCCUGCUUAAGCAGCUAUCAAAAAGCCCA-CU Clone SO_VWFR9.3:
                                         (SEQ ID NO: 69)
AUCGCGCUCUCCUGCUUAAGCAGCUAUCAAAUAG-CCCAUCUU Clone SO_VWFR9.14:
                                         (SEQ ID NO: 70)
UGGACGAACUGCCCUCAGCUACUUUCAUGUUGC-UGACGCA Clone SO_VWFR9.2:
                                         (SEQ ID NO: 71)
UAUACCACAGCCUGAGAUUAACCACCAACCCAGGA-CU
```

For use in biological systems (e.g., in vitro assays and in vivo models), the modified ribonucleotides may be replaced by 2'-O-methyl modified bases. The aptamers modulate biological activity in functional assays.

The Platelet Function Analyzer (PFA-100)

The PFA-100 is a bench-top instrument that uses whole blood and simulates platelet function under high shear stress conditions. Here, disposable cartridges coated with collagen/ADP were filled with 840 µl of whole human blood (collected in 10 ml sodium heparin tubes) and placed into the PFA-100. The standard test protocol was followed and each dilution point is done in duplicates.

During the assay, blood in the cartridge is aspirated under constant negative pressure from the reservoir, through a capillary, and passes a microscopic aperture cut into the membrane. The shear stress rate during this process reaches 5000-6000 s$^{-1}$ and, along with the platelet activators (i.e., collagen/ADP) present on the membrane, platelet activation, adhesion, and aggregation are initiated. These processes cause the formation of a platelet plug on the microscopic aperture and blood flow through the capillary ceases. The platelet function is measured as the time it takes to form the aperture occlusion. Although the PFA-100 is sensitive to many variables that affect platelet function, a number of studies revealed that it is most sensitive to certain platelet receptor defects (mainly GPIb-IX-V and GP IIbIIIa) and VWF defects.

Figure 18:
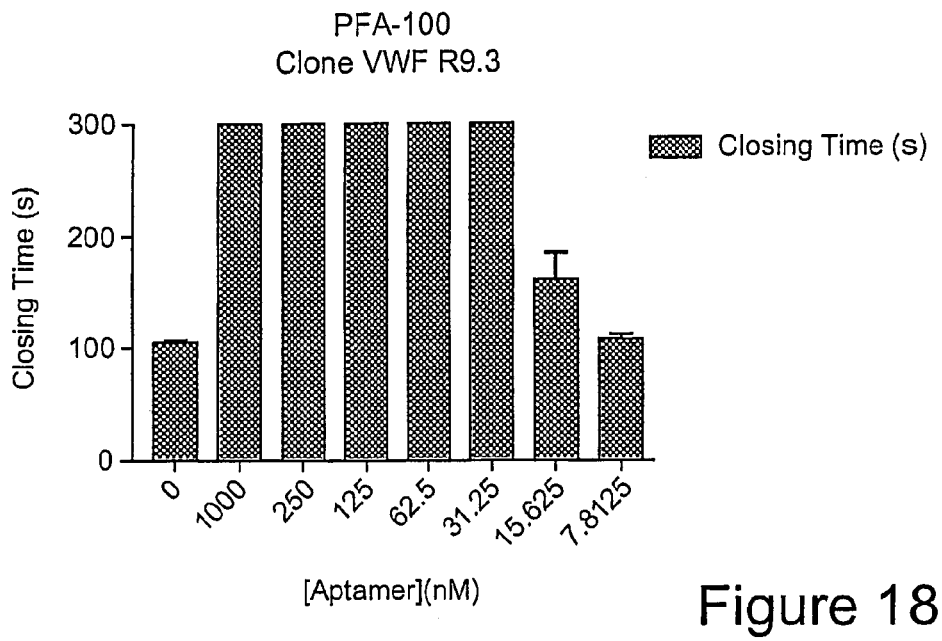
FIG. 18 shows a functional assay (i.e., inhibition of plug formation) used to demonstrate that VWF R9.3 modulates platelet function.

Clone VWF R9.3 ($K_d$ of about 1.3 nmoles and $B_{max}$ of about 57%) inhibited platelet plug formation completely in the PFA-100 at a concentration from 1000 nM to 31.25 nM (FIG. 18 and Table 2).

TABLE 2

Clone VWF R9.3 PFA-100 Data

| [Aptamer](nM) | Closure Time(s) | Closure Time(s) |
|---|---|---|
| 0 | 106 (baseline) | 103 (baseline) |
| 1000 | 300 (max value) | 300 (max value) |
| 250 | 300 | 300 |
| 125 | 300 | 300 |
| 62.5 | 300 | 300 |
| 31.25 | 300 | 300 |
| 15.625 | 185 | 138 |
| 7.8125 | 103 | 112 |

Ristocetin Induced Platelet Aggregation (RIPA) (VWF Specific Assay)

Platelet aggregation is the "gold standard" of platelet function testing and it is the most widely used functional assay for determining platelet defects. Here, a multichannel aggregometer (Chrono-log Corp.) and ristocetin agonist were used to evaluate biological activity of platelet rich plasma (PRP) obtained from citrated whole human blood. PRP (400 µl) was added to each cuvette, where it is stirred at 37° C. between the light source and the receptor. After the addition of ristocetin, an agonist known to cause platelet aggregation by initiating a bond between VWF molecules in plasma and GP Ib-IX-V receptors on platelet): platelets aggregate and begin to sediment to the bottom of the cuvette, and light transmission increases. The data is collected as percentage (%) increase in light transmission compared to control plasma.

Figure 19:
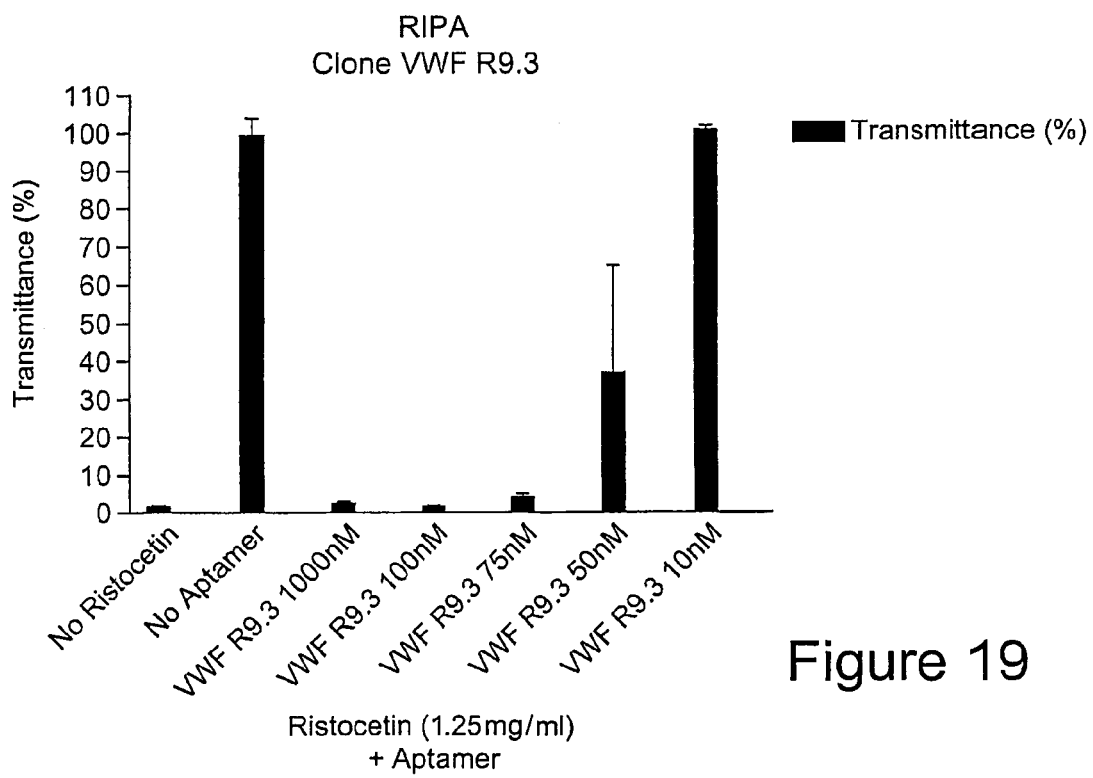
FIG. 19 shows a functional assay (i.e., platelet aggregation) used to demonstrate that VWF R9.3 modulates platelet function.

Clone VWF R9.3 inhibited platelet aggregation completely (transmittance of about 0-5%) in RIPA at a concentration from 1000 nM to 75 nM (FIG. 19 and Table 3).

TABLE 3

Clone VWF R9.3 RIPA Data

| [Ristocetin] (1.25 mg/ml) | Transmittance (%) | Transmittance (%) |
|---|---|---|
| No Ristocetin | 2.0 | 1.0 |
| No Aptamer | 104.0 | 95.0 |
| VWF R9.3 (1000 nM) | 3.0 | 2.0 |
| VWF R9.3 (100 nM) | 2.0 | 1.0 |
| VWF R9.3 (75 nM) | 5.0 | 3.0 |
| VWF R9.3 (50 nM) | 65.0 | 9.0 |
| VWF R9.3 (10 nM) | 102.0 | 100.0 |

Patents, patent applications, books, and other publications cited herein are incorporated by reference in their entirety.

In stating a numerical range, it should be understood that all values within the range are also described (e.g., one to ten also includes every integer value between one and ten as well as all intermediate ranges such as two to ten, one to five, and three to eight). The term "about" may refer to the statistical uncertainty associated with a measurement or the variability in a numerical quantity which a person skilled in the art would understand does not affect operation of the invention or its patentability.

All modifications and substitutions that come within the meaning of the claims and the range of their legal equivalents are to be embraced within their scope. A claim using the transition "comprising" allows the inclusion of other elements to be within the scope of the claim; the invention is also described by such claims using the transitional phrase "consisting essentially of" (i.e., allowing the inclusion of other elements to be within the scope of the claim if they do not materially affect operation of the invention) and the transition "consisting" (i.e., allowing only the elements listed in the claim other than impurities or inconsequential activities which are ordinarily associated with the invention) instead of the "comprising" term. Any of these three transitions can be used to claim the invention.

It should be understood that an element described in this specification should not be construed as a limitation of the claimed invention unless it is explicitly recited in the claims. Thus, the granted claims are the basis for determining the scope of legal protection instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be aspects of the invention. Similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

We claim:

1. An isolated aptamer comprised of a sequence selected from the group consisting of SEQ ID NO: 66, SEQ ID NO: 67, SEQ ID NO: 68, SEQ ID NO: 69, SEQ ID NO: 70, and SEQ ID NO: 71; which contains one or more modified bases, sugars, and/or phosphodiester linkages.

2. A composition comprising the aptamer of claim 1 and a vehicle.

3. A method of using the aptamer of claim 1, the method comprising modulating biological activity of von Willebrand Factor (VWF) in vitro or in vivo by binding between the aptamer and the VWF.

4. The method according to claim 3 further comprising binding between the aptamer and an oligonucleotide of complementary sequence.

5. An oligonucleotide which is complementary to a sequence of the aptamer of claim 1.

6. A method of using at least one aptamer of claim 1, the method comprising administering an effective amount of the at least one aptamer to a subject to inhibit biological activity of von Willebrand Factor (VWF).

7. The method according to claim 6 further comprising administering an effective amount of an oligonucleotide which is complementary to the sequence of the at least one aptamer to the subject.

8. A method of making a pharmaceutical composition, the method comprising formulating at least the aptamer of claim 1 and a vehicle to make the composition.

9. An isolated aptamer comprised of a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, and SEQ ID NO: 49; which contains one or more modified bases, sugars, and/or phosphodiester linkages.

* * * * *

SEQUENCE LISTING

```
<160> NUMBER OF SEQ ID NOS: 71

<210> SEQ ID NO 1
<211> LENGTH: 40
<212> TYPE: RNA
<213> ORGANISM: Artificial Sequence
<220> FEATURE:
<223> OTHER INFORMATION: random region of clones 17-1, 17-2, 17-4, 17-5,
      17-6, 17-10, 17-13, 17-14, 7S-1, 7S-16, 7S-18, 7S-19 and 7S-20

<400> SEQUENCE: 1
acuccuccaa gcgaccaaca ucggucccgu uucagaucaa                             40

<210> SEQ ID NO 2
<211> LENGTH: 40
<212> TYPE: RNA
<213> ORGANISM: Artificial Sequence
<220> FEATURE:
<223> OTHER INFORMATION: random region of clone 17-8

<400> SEQUENCE: 2
acuccuccaa gcgaccaaca ucggucccgc uucagaucaa                             40

<210> SEQ ID NO 3
<211> LENGTH: 40
<212> TYPE: RNA
<213> ORGANISM: Artificial Sequence
<220> FEATURE:
<223> OTHER INFORMATION: random region of clone 17-11

<400> SEQUENCE: 3
acuccuccaa gugaccaaca ucggucccgu uucagaucaa                             40

<210> SEQ ID NO 4
<211> LENGTH: 41
<212> TYPE: RNA
<213> ORGANISM: Artificial Sequence
<220> FEATURE:
<223> OTHER INFORMATION: random region of clone 7S-6
<220> FEATURE:
<221> NAME/KEY: misc_feature
<222> LOCATION: (12)..(12)
<223> OTHER INFORMATION: n is a, c, g, or u

<400> SEQUENCE: 4
acuccuccaa gncgaccaac aucggucccg uuucagauca a                           41

<210> SEQ ID NO 5
<211> LENGTH: 42
<212> TYPE: RNA
```

-continued

```
<213> ORGANISM: Artificial Sequence
<220> FEATURE:
<223> OTHER INFORMATION: random region of clones 7S-4, 7S-5 and 7S-7
<220> FEATURE:
<221> NAME/KEY: misc_feature
<222> LOCATION: (13)..(13)
<223> OTHER INFORMATION: n is a, c, g, or u

<400> SEQUENCE: 5
cacuccucca agncgaccaa caucggoccc guuucagauc aa                           42

<210> SEQ ID NO 6
<211> LENGTH: 41
<212> TYPE: RNA
<213> ORGANISM: Artificial Sequence
<220> FEATURE:
<223> OTHER INFORMATION: random region of clones 7S-8, 7S-9, 7S-10 and
      7S-11

<400> SEQUENCE: 6
cacuccucca agcgaccaac aucggucccg uuucagauca a                            41

<210> SEQ ID NO 7
<211> LENGTH: 41
<212> TYPE: RNA
<213> ORGANISM: Artificial Sequence
<220> FEATURE:
<223> OTHER INFORMATION: random region of clone 7S-15

<400> SEQUENCE: 7
uacuccucca agcgaccaac aucggucccg uuucagauca a                            41

<210> SEQ ID NO 8
<211> LENGTH: 40
<212> TYPE: RNA
<213> ORGANISM: Artificial Sequence
<220> FEATURE:
<223> OTHER INFORMATION: random region of clone 17-7

<400> SEQUENCE: 8
caaccagacu ccucaagcgu caccagaccc gacaacacca                              40

<210> SEQ ID NO 9
<211> LENGTH: 40
<212> TYPE: RNA
<213> ORGANISM: Artificial Sequence
<220> FEATURE:
<223> OTHER INFORMATION: random region of clone 17-12

<400> SEQUENCE: 9
cucuguuuga acccgcacuc gacacuuucc gagcucucac                              40

<210> SEQ ID NO 10
<211> LENGTH: 40
<212> TYPE: RNA
<213> ORGANISM: Artificial Sequence
<220> FEATURE:
<223> OTHER INFORMATION: random region of clones 7S-2 and 7S-3

<400> SEQUENCE: 10
agaaugaccc gaugagguac gccacgacug cccacuucuu                              40

<210> SEQ ID NO 11
<211> LENGTH: 42
<212> TYPE: RNA
<213> ORGANISM: Artificial Sequence
<220> FEATURE:
<223> OTHER INFORMATION: random region of clone 7S-13
```

```
<220> FEATURE:
<221> NAME/KEY: misc_feature
<222> LOCATION: (3)..(3)
<223> OTHER INFORMATION: n is a, c, g, or u

<400> SEQUENCE: 11
canaauguac ccgaugaggu acgccacgac ugcccacuuc uu                          42

<210> SEQ ID NO 12
<211> LENGTH: 40
<212> TYPE: RNA
<213> ORGANISM: Artificial Sequence
<220> FEATURE:
<223> OTHER INFORMATION: random region of clones 7K-2 and 7K-4

<400> SEQUENCE: 12
acuggcuagc uaaccaaugg uggauaugag uaccuugggc                             40

<210> SEQ ID NO 13
<211> LENGTH: 40
<212> TYPE: RNA
<213> ORGANISM: Artificial Sequence
<220> FEATURE:
<223> OTHER INFORMATION: random region of clones 7K-3, 7K-7, 7K-9,
      7K-10, 7K-11, 7K-13, 7K-14, 7K-15, 7K-16, 7K-17, 7K-20, 7K-22,
      7K-23, 7K-24, 7K-103, 7K-110, 7K-114, 7K-123, 7K-124 and 7K-125

<400> SEQUENCE: 13
ucucugggcu cuuaggagaa cggauaggag ugugcucgcu                             40

<210> SEQ ID NO 14
<211> LENGTH: 40
<212> TYPE: RNA
<213> ORGANISM: Artificial Sequence
<220> FEATURE:
<223> OTHER INFORMATION: random region of clone 7K-18

<400> SEQUENCE: 14
acucugggcu cuuaggagaa cggauaggag ugugcucgcu                             40

<210> SEQ ID NO 15
<211> LENGTH: 41
<212> TYPE: RNA
<213> ORGANISM: Artificial Sequence
<220> FEATURE:
<223> OTHER INFORMATION: random region of clone 7K-121

<400> SEQUENCE: 15
uccucugggc ucuuaggaga acggauagga gugugcucgc u                           41

<210> SEQ ID NO 16
<211> LENGTH: 40
<212> TYPE: RNA
<213> ORGANISM: Artificial Sequence
<220> FEATURE:
<223> OTHER INFORMATION: random region of clones 9D-14, 9D-16, 9D-16,
      9D-22, 9D-27 and 9D-29

<400> SEQUENCE: 16
ucgaucacac aguucaaacg uaauaagcca auguacgagg                             40

<210> SEQ ID NO 17
<211> LENGTH: 40
<212> TYPE: RNA
<213> ORGANISM: Artificial Sequence
<220> FEATURE:
<223> OTHER INFORMATION: random region of clone 9D-9
<220> FEATURE:
```

<221> NAME/KEY: misc_feature
<222> LOCATION: (1)..(1)
<223> OTHER INFORMATION: n is a, c, g, or u

<400> SEQUENCE: 17
ncgaucacac aguucaaacg uaauaagcca auguacgagg         40

<210> SEQ ID NO 18
<211> LENGTH: 41
<212> TYPE: RNA
<213> ORGANISM: Artificial Sequence
<220> FEATURE:
<223> OTHER INFORMATION: random region of clone 9D-30

<400> SEQUENCE: 18
uccgaucaca caguucaaac guaauaagcc aauguacgag g         41

<210> SEQ ID NO 19
<211> LENGTH: 40
<212> TYPE: RNA
<213> ORGANISM: Artificial Sequence
<220> FEATURE:
<223> OTHER INFORMATION: random region of clone 9K-9

<400> SEQUENCE: 19
ucgaucacac aguucaaacg uaauaagcca augcacgagg         40

<210> SEQ ID NO 20
<211> LENGTH: 40
<212> TYPE: RNA
<213> ORGANISM: Artificial Sequence
<220> FEATURE:
<223> OTHER INFORMATION: random region of clone 9K-22
<220> FEATURE:
<221> NAME/KEY: misc_feature
<222> LOCATION: (6)..(6)
<223> OTHER INFORMATION: n is a, c, g, or u

<400> SEQUENCE: 20
ucgaunacac aguucaaacg uaauaagcca auguacgagg         40

<210> SEQ ID NO 21
<211> LENGTH: 40
<212> TYPE: RNA
<213> ORGANISM: Artificial Sequence
<220> FEATURE:
<223> OTHER INFORMATION: random region of clone 7K-21 (Tog 25 consensus)

<400> SEQUENCE: 21
aacaaagcug uaguacuuac cgccaacccu ccaacccgac         40

<210> SEQ ID NO 22
<211> LENGTH: 40
<212> TYPE: RNA
<213> ORGANISM: Artificial Sequence
<220> FEATURE:
<223> OTHER INFORMATION: random region of clones 7K-84, 9K-15 and 7K-105

<400> SEQUENCE: 22
cgcgacagau cguauaauag ucaacgcucu aaccaaucac         40

<210> SEQ ID NO 23
<211> LENGTH: 42
<212> TYPE: RNA
<213> ORGANISM: Artificial Sequence
<220> FEATURE:
<223> OTHER INFORMATION: random region of clone 7K-28
<220> FEATURE:

<220> FEATURE:
<221> NAME/KEY: misc_feature
<222> LOCATION: (9)..(9)
<223> OTHER INFORMATION: n is a, c, g, or u

<400> SEQUENCE: 23
cccgacagna uacguauaau agucaacgcu cuaaccaauc ac           42

<210> SEQ ID NO 24
<211> LENGTH: 41
<212> TYPE: RNA
<213> ORGANISM: Artificial Sequence
<220> FEATURE:
<223> OTHER INFORMATION: random region of clone 7K-90

<400> SEQUENCE: 24
cgcgacagua ucguauaaua gucaacgcuc uaaccaauca c            41

<210> SEQ ID NO 25
<211> LENGTH: 40
<212> TYPE: RNA
<213> ORGANISM: Artificial Sequence
<220> FEATURE:
<223> OTHER INFORMATION: random region of clone 9D-11

<400> SEQUENCE: 25
cgagccggac uucagccagu gauaugaugc gacacacugc              40

<210> SEQ ID NO 26
<211> LENGTH: 39
<212> TYPE: RNA
<213> ORGANISM: Artificial Sequence
<220> FEATURE:
<223> OTHER INFORMATION: random region of clone 7K-58

<400> SEQUENCE: 26
gccaaggacc gaggcccaa cugacaguuu caacaagcg               39

<210> SEQ ID NO 27
<211> LENGTH: 41
<212> TYPE: RNA
<213> ORGANISM: Artificial Sequence
<220> FEATURE:
<223> OTHER INFORMATION: random region of clone 7K-101
<220> FEATURE:
<221> NAME/KEY: misc_feature
<222> LOCATION: (8)..(8)
<223> OTHER INFORMATION: n is a, c, g, or u

<400> SEQUENCE: 27
gccaaggnac cgaggccacc aacugacagu uucaacaagc g            41

<210> SEQ ID NO 28
<211> LENGTH: 40
<212> TYPE: RNA
<213> ORGANISM: Artificial Sequence
<220> FEATURE:
<223> OTHER INFORMATION: random region of clones 7K-5, 7K-60 and 9K-14

<400> SEQUENCE: 28
acaucuccgc acucaguuug agcaccaaac caacagcucc              40

<210> SEQ ID NO 29
<211> LENGTH: 41
<212> TYPE: RNA
<213> ORGANISM: Artificial Sequence
<220> FEATURE:
<223> OTHER INFORMATION: random region of clone 10S-14
<220> FEATURE:

```
<221> NAME/KEY: misc_feature
<222> LOCATION: (1)..(1)
<223> OTHER INFORMATION: n is a, c, g, or u

<400> SEQUENCE: 29
nacaucuccg cacucaguuu gagcaccaaa ccaacagcuc c                    41

<210> SEQ ID NO 30
<211> LENGTH: 41
<212> TYPE: RNA
<213> ORGANISM: Artificial Sequence
<220> FEATURE:
<223> OTHER INFORMATION: random region of clones 9D-1 and 7K-100

<400> SEQUENCE: 30
cacaucuccg cacucaguuu gagcaccaaa ccaacagcuc c                    41

<210> SEQ ID NO 31
<211> LENGTH: 40
<212> TYPE: RNA
<213> ORGANISM: Artificial Sequence
<220> FEATURE:
<223> OTHER INFORMATION: random region of clone 7K-130

<400> SEQUENCE: 31
ccaucuccgc acucaguuug agcaccaaac caacagcucc                      40

<210> SEQ ID NO 32
<211> LENGTH: 41
<212> TYPE: RNA
<213> ORGANISM: Artificial Sequence
<220> FEATURE:
<223> OTHER INFORMATION: random region of clones 9K-10, 9K-19, 7K-31 and
      10S-18

<400> SEQUENCE: 32
caccuagcgc gcuugacgug gccccuucgc agguccugga u                    41

<210> SEQ ID NO 33
<211> LENGTH: 42
<212> TYPE: RNA
<213> ORGANISM: Artificial Sequence
<220> FEATURE:
<223> OTHER INFORMATION: random region of clone 9D-24
<220> FEATURE:
<221> NAME/KEY: misc_feature
<222> LOCATION: (1)..(1)
<223> OTHER INFORMATION: n is a, c, g, or u

<400> SEQUENCE: 33
naccuagccg cgcuugacgu ggccccuucg cagguccugg au                   42

<210> SEQ ID NO 34
<211> LENGTH: 40
<212> TYPE: RNA
<213> ORGANISM: Artificial Sequence
<220> FEATURE:
<223> OTHER INFORMATION: random region of clone 9D-18

<400> SEQUENCE: 34
accuagcgcg cuugacgugg ccccuucgca gguccuggau                      40

<210> SEQ ID NO 35
<211> LENGTH: 39
<212> TYPE: RNA
<213> ORGANISM: Artificial Sequence
<220> FEATURE:
<223> OTHER INFORMATION: random region of clone 10S-8
```

```
<400> SEQUENCE: 35
ucuagcucua gccccugauu acuuaaagug aucacacag                              39

<210> SEQ ID NO 36
<211> LENGTH: 41
<212> TYPE: RNA
<213> ORGANISM: Artificial Sequence
<220> FEATURE:
<223> OTHER INFORMATION: random region of clone 10S-20

<400> SEQUENCE: 36
gucuagccuc uagcccuga uuacuuaaag ugaucacaca g                            41

<210> SEQ ID NO 37
<211> LENGTH: 41
<212> TYPE: RNA
<213> ORGANISM: Artificial Sequence
<220> FEATURE:
<223> OTHER INFORMATION: random region of clone 10S-17

<400> SEQUENCE: 37
cauggccaug aaccagacac gcucgcccgu agccgguauu u                           41

<210> SEQ ID NO 38
<211> LENGTH: 42
<212> TYPE: RNA
<213> ORGANISM: Artificial Sequence
<220> FEATURE:
<223> OTHER INFORMATION: random region of clone 10S-23
<220> FEATURE:
<221> NAME/KEY: misc_feature
<222> LOCATION: (9)..(9)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 38
cauggcagna uuaaccagna cacacuccu gacccuuaa cc                            42

<210> SEQ ID NO 39
<211> LENGTH: 40
<212> TYPE: RNA
<213> ORGANISM: Artificial Sequence
<220> FEATURE:
<223> OTHER INFORMATION: random region of clone 10S-10
<220> FEATURE:
<221> NAME/KEY: misc_feature
<222> LOCATION: (17)..(17)
<223> OTHER INFORMATION: n is a, c, g, or u

<400> SEQUENCE: 39
cauggcucug aaccagnaca cguuaccucc gcacugacug                             40

<210> SEQ ID NO 40
<211> LENGTH: 39
<212> TYPE: RNA
<213> ORGANISM: Artificial Sequence
<220> FEATURE:
<223> OTHER INFORMATION: random region of clone 10S-7
<220> FEATURE:
<221> NAME/KEY: misc_feature
<222> LOCATION: (6)..(6)
<223> OTHER INFORMATION: n is a, c, g, or u

<400> SEQUENCE: 40
cauggncacg aaccagacgu cuaccucccu ccaccuugg                              39
```

<210> SEQ ID NO 41
<211> LENGTH: 40
<212> TYPE: RNA
<213> ORGANISM: Artificial Sequence
<220> FEATURE:
<223> OTHER INFORMATION: random region of clones 10S-11 and 10S-19

<400> SEQUENCE: 41
caugucauag uaaucagaca uguccuacc gcccacgauu                    40

<210> SEQ ID NO 42
<211> LENGTH: 40
<212> TYPE: RNA
<213> ORGANISM: Artificial Sequence
<220> FEATURE:
<223> OTHER INFORMATION: random region of clone 10S-13

<400> SEQUENCE: 42
caucguuagc caucacacga gucgcggcau gucacauaau                   40

<210> SEQ ID NO 43
<211> LENGTH: 40
<212> TYPE: RNA
<213> ORGANISM: Artificial Sequence
<220> FEATURE:
<223> OTHER INFORMATION: random region of clone 9D-26

<400> SEQUENCE: 43
cgugaauuca gccuccucua gugagcgagu ccagacacgc                   40

<210> SEQ ID NO 44
<211> LENGTH: 40
<212> TYPE: RNA
<213> ORGANISM: Artificial Sequence
<220> FEATURE:
<223> OTHER INFORMATION: random region of clone 9D-6

<400> SEQUENCE: 44
acuugucgga uaggcccuga uccuaguaca caagaccaag                   40

<210> SEQ ID NO 45
<211> LENGTH: 41
<212> TYPE: RNA
<213> ORGANISM: Artificial Sequence
<220> FEATURE:
<223> OTHER INFORMATION: random region of clone 9D-31

<400> SEQUENCE: 45
cacuugucgg auaggcccug auccuaguac acaagaccaa g                 41

<210> SEQ ID NO 46
<211> LENGTH: 41
<212> TYPE: RNA
<213> ORGANISM: Artificial Sequence
<220> FEATURE:
<223> OTHER INFORMATION: random region of clone 9D-15

<400> SEQUENCE: 46
acuugucgga uaggcccuga uccuaguaca caaguaccaa g                 41

<210> SEQ ID NO 47
<211> LENGTH: 46
<212> TYPE: RNA
<213> ORGANISM: Artificial Sequence
<220> FEATURE:
<223> OTHER INFORMATION: random region of clone 9D-20

```
<220> FEATURE:
<221> NAME/KEY: misc_feature
<222> LOCATION: (1)..(1)
<223> OTHER INFORMATION: n is a, c, g, or u

<400> SEQUENCE: 47
nacuugucgg uauaggcccu guauccuagu uacacaagua ccaagu          46

<210> SEQ ID NO 48
<211> LENGTH: 46
<212> TYPE: RNA
<213> ORGANISM: Artificial Sequence
<220> FEATURE:
<223> OTHER INFORMATION: random region of clone 9D-10

<400> SEQUENCE: 48
cacuuguacg gcauagggcc cugcauccua guacacaagc accaag          46

<210> SEQ ID NO 49
<211> LENGTH: 40
<212> TYPE: RNA
<213> ORGANISM: Artificial Sequence
<220> FEATURE:
<223> OTHER INFORMATION: random region of clone 7K-41
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u

<400> SEQUENCE: 49
acuccangac aaucgucunc auccauauag ccuguccacu               40

<210> SEQ ID NO 50
<211> LENGTH: 40
<212> TYPE: RNA
<213> ORGANISM: Artificial Sequence
<220> FEATURE:
<223> OTHER INFORMATION: random region of clone 10S-4

<400> SEQUENCE: 50
cacguuacac auuuggccuc acaaccaaag cccucccaga               40

<210> SEQ ID NO 51
<211> LENGTH: 40
<212> TYPE: RNA
<213> ORGANISM: Artificial Sequence
<220> FEATURE:
<223> OTHER INFORMATION: random region of clone 10S-5

<400> SEQUENCE: 51
cacguuacac auuuggccuc acaaccaaag cccuccuuga               40

<210> SEQ ID NO 52
<211> LENGTH: 43
<212> TYPE: RNA
<213> ORGANISM: Artificial Sequence
<220> FEATURE:
<223> OTHER INFORMATION: random region of clone 10S-6
<220> FEATURE:
<221> NAME/KEY: misc_feature
<222> LOCATION: (12)..(12)
<223> OTHER INFORMATION: n is a, c, g, or u
<220> FEATURE:
<221> NAME/KEY: misc_feature
<222> LOCATION: (23)..(23)
<223> OTHER INFORMATION: n is a, c, g, or u
```

```
<220> FEATURE:
<221> NAME/KEY: misc_feature
<222> LOCATION: (27)..(27)
<223> OTHER INFORMATION: n is a, c, g, or u
<220> FEATURE:
<221> NAME/KEY: misc_feature
<222> LOCATION: (31)..(31)
<223> OTHER INFORMATION: n is a, c, g, or u

<400> SEQUENCE: 52
cacguuacac anuugggcaa ggngauncac nacccugcuc uaa                43

<210> SEQ ID NO 53
<211> LENGTH: 43
<212> TYPE: RNA
<213> ORGANISM: Artificial Sequence
<220> FEATURE:
<223> OTHER INFORMATION: random region of clone 10S-16

<400> SEQUENCE: 53
cacguacaaa cacauggaag uaaauccagc cccucccaau gac                43

<210> SEQ ID NO 54
<211> LENGTH: 40
<212> TYPE: RNA
<213> ORGANISM: Artificial Sequence
<220> FEATURE:
<223> OTHER INFORMATION: random region of clones 7K-85, 9K-5 and 9K-8

<400> SEQUENCE: 54
cacguuacac auuuggccuc acaaccaaag cccuccuuga                    40

<210> SEQ ID NO 55
<211> LENGTH: 40
<212> TYPE: RNA
<213> ORGANISM: Artificial Sequence
<220> FEATURE:
<223> OTHER INFORMATION: random region of clone 7K-6

<400> SEQUENCE: 55
guccugguug uagcgccucg acaacugacu caauccuggc                    40

<210> SEQ ID NO 56
<211> LENGTH: 40
<212> TYPE: RNA
<213> ORGANISM: Artificial Sequence
<220> FEATURE:
<223> OTHER INFORMATION: random region of clone 7K-8

<400> SEQUENCE: 56
auggugcagu cguacggaua ccuacucuga accucuuccc                    40

<210> SEQ ID NO 57
<211> LENGTH: 40
<212> TYPE: RNA
<213> ORGANISM: Artificial Sequence
<220> FEATURE:
<223> OTHER INFORMATION: random region of clone 7K-19

<400> SEQUENCE: 57
aucuucggca caacagacca cuguccucug gccagcgaaa                    40

<210> SEQ ID NO 58
<211> LENGTH: 41
<212> TYPE: RNA
<213> ORGANISM: Artificial Sequence
<220> FEATURE:
<223> OTHER INFORMATION: random region of clone 7K-43
```

```
<400> SEQUENCE: 58
gcacaucucg aagaugcuag ccgauauacg ccacagugug c                         41

<210> SEQ ID NO 59
<211> LENGTH: 40
<212> TYPE: RNA
<213> ORGANISM: Artificial Sequence
<220> FEATURE:
<223> OTHER INFORMATION: random region of clone 7K-48

<400> SEQUENCE: 59
gacaucucga agaugcuagc cgauauacgc cacagugugc                           40

<210> SEQ ID NO 60
<211> LENGTH: 41
<212> TYPE: RNA
<213> ORGANISM: Artificial Sequence
<220> FEATURE:
<223> OTHER INFORMATION: random region of clone 7K-89
<220> FEATURE:
<221> NAME/KEY: misc_feature
<222> LOCATION: (1)..(1)
<223> OTHER INFORMATION: n is a, c, g, or u

<400> SEQUENCE: 60
ncacaucucg aagaugcuag ccgauauacg ccacagugug c                         41

<210> SEQ ID NO 61
<211> LENGTH: 39
<212> TYPE: RNA
<213> ORGANISM: Artificial Sequence
<220> FEATURE:
<223> OTHER INFORMATION: random region of clone 10S-9

<400> SEQUENCE: 61
cacagcguag ccuauaauac ccgacggccc aacucccua                            39

<210> SEQ ID NO 62
<211> LENGTH: 41
<212> TYPE: RNA
<213> ORGANISM: Artificial Sequence
<220> FEATURE:
<223> OTHER INFORMATION: random region of clone 10S-12

<400> SEQUENCE: 62
cacacuccgu gaaccacacg accaauucuc cgcgccucgc c                         41

<210> SEQ ID NO 63
<211> LENGTH: 40
<212> TYPE: RNA
<213> ORGANISM: Artificial Sequence
<220> FEATURE:
<223> OTHER INFORMATION: random region of clone 7K-55

<400> SEQUENCE: 63
caaucgaaug ucuugccgac cgauagucau acgagacuau                           40

<210> SEQ ID NO 64
<211> LENGTH: 40
<212> TYPE: RNA
<213> ORGANISM: Artificial Sequence
<220> FEATURE:
<223> OTHER INFORMATION: random region of clone 7K-116

<400> SEQUENCE: 64
acccauugac gacuaugucg caccacaucg ccucaauggc                           40
```

```
<210> SEQ ID NO 65
<211> LENGTH: 39
<212> TYPE: RNA
<213> ORGANISM: Artificial Sequence
<220> FEATURE:
<223> OTHER INFORMATION: random region of clone 7K-128

<400> SEQUENCE: 65
ucagcacguc ugcgcccuac gcagaggcuc gucguccca                                39

<210> SEQ ID NO 66
<211> LENGTH: 40
<212> TYPE: RNA
<213> ORGANISM: Artificial Sequence
<220> FEATURE:
<223> OTHER INFORMATION: random region of clone FM10

<400> SEQUENCE: 66
aucgcgcucu ccugcuuaag cagcuaucaa auagcccacu                               40

<210> SEQ ID NO 67
<211> LENGTH: 40
<212> TYPE: RNA
<213> ORGANISM: Artificial Sequence
<220> FEATURE:
<223> OTHER INFORMATION: random region of clone Q_W3-6

<400> SEQUENCE: 67
accgcgcucu ccugcuuaag cagcuaucaa auagcccacu                               40

<210> SEQ ID NO 68
<211> LENGTH: 40
<212> TYPE: RNA
<213> ORGANISM: Artificial Sequence
<220> FEATURE:
<223> OTHER INFORMATION: random region of clone Q-W1-9

<400> SEQUENCE: 68
aucgcgcucu ccugcuuaag cagcuaucaa aaagcccacu                               40

<210> SEQ ID NO 69
<211> LENGTH: 42
<212> TYPE: RNA
<213> ORGANISM: Artificial Sequence
<220> FEATURE:
<223> OTHER INFORMATION: random region of clone SO_VWFR9.3

<400> SEQUENCE: 69
aucgcgcucu ccugcuuaag cagcuaucaa auagcccauc uu                            42

<210> SEQ ID NO 70
<211> LENGTH: 40
<212> TYPE: RNA
<213> ORGANISM: Artificial Sequence
<220> FEATURE:
<223> OTHER INFORMATION: random region of clone SO_VWFR9.14

<400> SEQUENCE: 70
uggacgaacu gcccucagcu acuuucaugu ugcugacgca                               40
```

```
<210> SEQ ID NO 71
<211> LENGTH: 37
<212> TYPE: RNA
<213> ORGANISM: Artificial Sequence
<220> FEATURE:
<223> OTHER INFORMATION: random region of clone SO_VWFR9.2

<400> SEQUENCE: 71
uauaccacag ccugagauua accaccaacc caggacu                                    37
```